(12) United States Patent
Lewis et al.

(10) Patent No.: US 9,254,287 B2
(45) Date of Patent: Feb. 9, 2016

(54) THERAPEUTIC FORMULATION AND METHODS OF TREATMENT

(71) Applicant: MacuCLEAR, Inc., Plano, TX (US)

(72) Inventors: Pamela A. Lewis, Bergheim, TX (US); William H. Woller, San Antonio, TX (US)

(73) Assignee: MacuCLEAR, Inc., Richardson, TX (US)

( * ) Notice: Subject to any disclaimer, the term of this patent is extended or adjusted under 35 U.S.C. 154(b) by 0 days.

(21) Appl. No.: 13/912,149

(22) Filed: Jun. 6, 2013

(65) Prior Publication Data

US 2013/0331393 A1    Dec. 12, 2013

Related U.S. Application Data

(60) Provisional application No. 61/658,304, filed on Jun. 11, 2012.

(51) Int. Cl.
*A61K 31/502*     (2006.01)
*A61K 9/00*       (2006.01)

(52) U.S. Cl.
CPC ............. *A61K 31/502* (2013.01); *A61K 9/0048* (2013.01)

(58) Field of Classification Search
CPC .................................................. A61K 31/502
See application file for complete search history.

(56) References Cited

U.S. PATENT DOCUMENTS

| | | | |
|---|---|---|---|
| 4,055,645 | A | 10/1977 | Scriabine |
| 4,865,599 | A | 9/1989 | Chiou et al. |
| 5,252,607 | A | 10/1993 | Chiou |
| 5,422,116 | A | 6/1995 | Yen et al. |
| 5,459,133 | A | 10/1995 | Neufeld |
| 5,475,033 | A | 12/1995 | Ohmori et al. |
| 5,500,230 | A | 3/1996 | Nathanson |
| 5,596,011 | A | 1/1997 | Repine et al. |
| 5,698,155 | A | 12/1997 | Grosswald et al. |
| 6,028,099 | A | 2/2000 | DeJuan, Jr. |
| 6,066,675 | A | 5/2000 | Wen et al. |
| 6,294,544 | B1 | 9/2001 | Araie et al. |
| 6,313,155 | B1 | 11/2001 | Sponsel |
| 6,451,799 | B1 | 9/2002 | Ogawa et al. |
| 6,692,759 | B1 | 2/2004 | Wong et al. |
| 8,088,773 | B2 | 1/2012 | Chiou |
| 8,318,741 | B2 | 11/2012 | Chiou |
| 2002/0119974 | A1 | 8/2002 | Laties |
| 2003/0171375 | A1 | 9/2003 | Brazzel |
| 2004/0214215 | A1 | 10/2004 | Yu et al. |
| 2005/0059744 | A1 | 3/2005 | Donello et al. |
| 2008/0300292 | A1 | 12/2008 | Letts et al. |
| 2009/0012057 | A1 | 1/2009 | Garvey |

FOREIGN PATENT DOCUMENTS

| | | |
|---|---|---|
| EP | 0265042 A | 4/1988 |
| JP | 2004-250347 A | 9/2004 |
| RU | 2107497 C1 | 3/1998 |
| WO | WO 98/10758 A1 | 3/1998 |
| WO | WO 00/52479 A2 | 9/2000 |
| WO | WO 01/10406 A2 | 2/2001 |
| WO | WO 2004/042353 A2 | 5/2004 |

OTHER PUBLICATIONS

Beauregard et al., "Effects of nitric oxide doners and nitric oxide synthase substrates on ciliary muscle contracted by carbachol and endothelin for possible use in myopia prevention", J. Ocular Pharm. Ther., vol. 17, No. 1, 3 pgs. (2004) *Abstract Only*, printed from http://www.liebertonline.com/doi/abs/10.1089/108076801750125577 on May 29, 2010.

Chiou, "Review: effects of nitric oxide on eye diseases and their treatment", J. Ocul. Pharmacol. Ther., vol. 17, No. 2, pp. 189-198 (2001).

Ciulla et al., "Color Doppler imaging discloses reduced ocular blood flow velocities in nonexudative age-related macular degeneration", Am. J. Opthalmol., vol. 128, No. 1, pp. 75-80 (1999).

Database WPI week 200138, Thomson Scienctific, London, GB; AN 2001-359955, JP2001072591A, Araya et al., Kowa Co., Ltd., Published Mar. 21, 2001 *Abstract only*.

Edwards et al., "Molecular genetics of AMD and current animal models", Angiogenesis, vol. 10, pp. 119-132 (2007).

Feigl et al., "Age-related maculopathy in the light of ischaemia", Clin. Exp. Optom., vol. 90, No. 4, pp. 263-271 (2007).

Feigl et al., "Functional loss in early age-related maculopathy; the ischaemia postreceptoral hypothesis", Eye, vol. 21, No. 6, pp. 689-696 (2007).

Friedman "Update of the vascular model of AMD", Br. J. Opthalmol., vol. 88, No. 2, pp. 161-163 (2004).

Grunwald et al., "Foveolar choroidal blood flow in age-related macular degeneration", Invest. Opthaimol. Vis. Sci., vol. 39, No. 2, pp. 385-390 (1998).

Grunwald et al., "Reduced foveolar choroidal blood flow in eyes with increasing AMD severity", Invest. Opthalmol. Vis. Sci., vol. 46, No. 3, pp, 1033-1038 (2005).

Harris et al., "The effects of dorzolamide on choroidal and retinal perfusion in non-exudative age related macular degeneration", Br J. Ophthamology, vol. 87, No. 6, pp. 753-757 (2003).

Macular Degeneration Partnership "What is AMD", www.AMD.org, 2pgs., Online Article printed from http://www.amd.org/what-is-amd.html on May 29, 2010.

Meszaros, "Dry AMD treatments promising", Opthalmology Times, vol. 36, No. 8, 2 pgs., Apr. 15, 2011.

Metelitsina et al., "Effect of systemic hypertension on foveolar choroidal blood flow in age related macular degeneration", Br. J. Opthalmol., vol. 90, No. 3, pp. 342-346 (2006).

Meteltsina et al., "Foveolar choroidal circulation and choroidal neovascularization in age-related macular degeneration", Invest. Opthalmol. Vis. Sci., vol. 49, No. 1, pp. 358-363 (2008).

(Continued)

*Primary Examiner* — Zohreh Fay

(74) *Attorney, Agent, or Firm* — Jacqueline F. Mahoney; Judy M. Mohr; McDermott Will & Emery LLP

(57) ABSTRACT

The present disclosure relates pharmaceutical formulations comprising hydralazine in the treatment of eye diseases and conditions with the formulations. The present disclosure also related to methods of preparing the pharmaceutical formulations.

15 Claims, 4 Drawing Sheets

(56) References Cited

OTHER PUBLICATIONS

Miyano et al., "Pharmacological prevention of ocular inflammation induced by lens proteins", Opthalmic. Res., vol. 16 No., pp. 256-263 (1984) *Abstract Only*.

Nathanson "Nitrovasodilators as a new class of ocular hypotensive agents", J. Pharmacol. Exp. Ther., vol. 260, No. 3, pp. 956-965 (1992).

O'Shea et al., "Age related macular degeneration-terminoloay", The Macular Disease Society, 9 pgs., Online Article printed from http://web.archive.org/web/20031222155235/http://medweb.bham.ac.uk/easdec/eyetextbook/AMD/armd.htm on Dec. 22, 2003.

Ralston et al., "A Pilot, Open-Label Study of the Safety of MC-1101 in Both Normal Volunteers and Patients With Early Nonexudative Age-Related Macular Degeneration", ARVO Presentation Abstract, Program/Poster No. 913/A196, 3 pgs. (2010) Online article printed from http://www.abstractsonline.com/plan/ViewAbstract.aspx?mID=2511&sKey=8d71b2af-2143-46c5-8ba1-81c043ba896c&cKey=1df0eda7-354b-4b0a-8449-99045b50e3af&mKey=%7B1EA90E66-C548-49E0-9F05-30DA7938D511%7D on Jul. 16, 2013.

Rigas et al., "Chorioidal vascular resistance in age-related macular degeneration", Invest. Opthalmoi. Vis. Sci., vol. 45, E-Abstract 31100, 3 pgs. (2004) printed from http://abstracts.iovs.org/cgi/content/abstract/45/5/3110 on Feb. 15, 2012.

Schmidt-Erfuth et al., "Management of neovascular age related macular degeneration", Prog. Ret. Eye Res. vol. 26, pp. 437-451 (2007).

Winfield, "Opthalmic products", Pharmaceutical Practice, Churchill Livingstone Edinburgh, New York, pp. 264-279 (2004).

Wright et al., "Improvement of vision in macular degeneration associated with intravenous zinc and selenium therapy: two cases", J. Nutr. Environ. Med., vol. 1, Issue 2, pp. 133-138 (1990).

Wu et al., "Neovascularization, Chloroidal", Medscape, 4 pos. (2010) Online article printed from http://emedicine.medscape.com/1190818-overview on Nov. 17, 2010.

Xuan et al., "Improvement of ocular blood flow and retinal functions with puerarin analogs", Ocular Pharma. Thera., vol. 15, No. 3, pp. 207-216 (1999).

Xuan and Chiou, "Release of nitric Oxide bt N-Nitropyrazoles in rabbit lacrimal gland cell culture", J. Ocular Pharma. Thera., vol. 19, No. 3, pp. 265-270 (2003).

Zou et al., "Pharmacological therapy in age-related macular degeneration (AMD)", Int. J. Ophthalmology, vol. 5, No. 1, pp. 8-18 (2005).

International Search Report from related PCT Patent Application No. PCT/US2013/044617 mailed on Sep. 19, 2013.

Effect of 1% hydralazine eye drops on rabbits choroidal blood flow with 40mmHg IOP

Effect of hydralazine on CNV area measured by fluorescein after 4W treatment

Effect of hydralazine on CNV area measured by choroidal flat mount

THERAPEUTIC FORMULATION AND METHODS OF TREATMENT

CROSS-REFERENCE TO RELATED APPLICATIONS

This application claims the benefit of U.S. Provisional Application No. 61/658,304, filed Jun. 11, 2012, which is incorporated herein by reference in its entirety.

TECHNICAL FIELD

The subject matter described herein relates to formulations and treatment of the eyes therewith.

BACKGROUND

Aging is a chronic process causing degeneration of cells, tissues, and organs, including choroidal blood vessels, retinal pigment epithelium cells (RPEC) and Bruch's membrane of the eye. Arteriosclerotic aging changes choroidal blood vessels, particularly the macular chorio-capillaris resulting in a decrease in total capillary blood flow. As a result, retinal pigment epithelium starts to accumulate drusen and lipofuscin, alters cell shape, density, pigmentation, lysosomal activity and extracellular matrix formation. Gradually, Bruch's membrane shows thickening and decreased permeability, resulting in breakdown that can allow choroidal neovascularization (CNV) to appear, which ultimately results in neovascular age-related macular degeneration (also wet age-related macular degeneration) and blindness. Clinical evidence has suggested that ischemia or decreases in choroidal blood flow may be associated with a number of serious retinal diseases, including age-related macular degeneration (AMD or ARMD) (Grunwald et al., 1998, Invest Ophthalmol Vis Sci., 39(2):385-390; Grunwald et al., 2005, Invest Ophthalmol Vis Sci., 46(3):1033-1038; Ciulla et al., 1999, Am J. Ophthalmol, 128(1):75-80; Metelitsina et al., 2006, Br J Ophthalmol, 90(3):342-346; Metelitsina et al., 2008, Invest Ophthalmol Vis Sci, 49(1):358-363). Both ocular and systemic vascular factors, such as systemic hypertension and ocular hypertension, are thought to play a role in the development of AMD and in choroidal neovascularization (Metelitsina 2006; Metelitsina 2008; U.S. Pat. No. 5,500,230 to Nathanson et al.). Thus, there is a need to identity agents that prevent choroidal neovascularization and/or increase choroidal blood flow.

Numerous methods have been attempted to treat age-related macular degeneration without success. They include laser photocoagulation for choroidal neovascularization, radiation treatment, transpupillary thermotherapy of subfoveal occult choroidal neovascularization, submacular surgery, limited macular translocation, adjuncts in surgery, argon laser to drusen, infrared diode laser photocoagulation for treatment of wet AMD. Recently, compositions for treating the non-neovascular or dry AMD comprising hypotensive agents, such as hydralazine, were described in U.S. Pat. No. 8,088,773 to Chiou, which is incorporated by reference herein.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, an ophthalmic composition is described. In one embodiment, the ophthalmic composition comprises a pharmaceutically active drug comprising hydralazine in an amount between about 0.02-2 wt %, and one or more of: one or more buffer solutions having a pH of between 3.5-4.5; one or more chelating agents; one or more isotonicity agents; one or more preservatives; one or more viscosity enhancers, and one or more diluents. In an embodiment, the composition has a pH of between 4.0-4.4. In another embodiment, the ophthalmic composition comprises a pharmaceutically active drug comprising hydralazine in an amount between about 0.02-2 wt %; an acetate buffer solution having pH of between 3.9-4.5 in an amount between 8-12 wt %; propylene glycol in an amount between 0.5-2 wt %; sodium chloride in an amount between 0.25-1 wt %; methylparaben in an amount between 0.015-0.06 wt %; benzalkonium chloride in the form of a 50% solution, present in an amount between 0.01-0.04 wt %; and edetate disodium in an amount between 0.008-0.030 wt %. In an embodiment, the composition has a pH of between 4.0-4.4.

The pharmaceutically active drug may comprise hydralazine hydrochloride. In another embodiment, the drug is present in an amount between 0.5-2 wt %.

In another embodiment, the acetate buffer solution has a pH of about 4.2 and is present in an amount of about 10 wt %. The acetate buffer solution may be comprised of sodium acetate and 2N acetic acid.

In an embodiment, propylene glycol is present is an amount of about 1 wt %. In another embodiment, methylparaben is present in an amount of about 0.03 wt %. In yet another embodiment, benzalkonium chloride is present in the form of a 50% solution and is present in an amount of about 0.02 wt %. In an additional embodiment, edetate disodium is present in an amount of about 0.015 wt %.

In another aspect, a method for preparing an ophthalmic formulation is contemplated. In one embodiment, the method comprises mixing a diluent and one or more buffer solutions having a pH between about 3.5 to 4.5 to form a first interim mixture, adding one or more chelating agents to the first interim mixture to form a second interim mixture, adding one or more lubricants to the second interim mixture to form a third interim mixture, adding one or more isotonicity agents to the third interim mixture to form a fourth interim mixture, adding one or more preservatives to the fourth interim mixture to form a fifth interim mixture, adding a pharmaceutically active drug comprising hydralazine to the fifth interim mixture to form the ophthalmic formulation.

In an embodiment, the buffer is an acetate buffer solution having a pH of about 3.9-4.5 which is added in an amount to provide between about 8-12 wt % of the acetate buffer solution in the formulation. In another embodiment, acetate buffer solution is added in an amount to provide about 10 wt % acetate buffer in the formulation. In a further embodiment, the acetate buffer solution is comprised of sodium acetate and 2N acetic acid.

In an embodiment, the chelating agent is edetate disodium, which is added in an amount to provide between about 0.008-0.030 wt % of edetate disodium in the formulation. In a further embodiment, edetate disodium is added in an amount to provide about 0.015 wt % edetate disodium in the formulation.

In an embodiment, the lubricant is propylene glycol added in an amount to provide between about 0.5-2 wt % of propylene glycol in the formulation. In a further embodiment, propylene glycol is added in an amount to provide about 15 wt % propylene glycol in the formulation.

In a further embodiment, the isotonicity agent is sodium chloride added in an amount to provide between about 0.25-1 wt % of sodium chloride in the formulation. In an embodiment, sodium chloride is added in an amount to provide about 0.5 wt % sodium chloride in the formulation.

In yet another embodiment, a preservative is benzalkonium chloride added in an amount to provide between about 0.01-0.04 wt % of benzalkonium chloride in the formulation. In another embodiment, benzalkonium chloride is added in an amount to provide about 0.02 wt % benzalkonium chloride in the formulation. In a further embodiment, a second preservative is added, where the second preservative is methylparaben added in an amount to provide between about 0.015-0.06 wt % of methylparaben in the formulation. In yet another embodiment, methylparaben is added in an amount to provide about 0.03 wt % methylparaben in the formulation.

In embodiments, the pharmaceutically active drug is hydralazine present in the formulation at between about 0.5-2 wt %. In further embodiments, the pharmaceutically active drug is hydralazine hydrochloride. In a particular embodiment, the pharmaceutically active drug is hydralazine hydrochloride present in the formulation at about 1 wt %.

In embodiments, one or more of the steps of adding further comprise mixing while adding.

In a further aspect, a method for treating a macular degeneration is contemplated. In embodiments, the method comprises administering to an eye of a subject at risk of or diagnosed with macular degeneration, an ophthalmic composition described herein or prepared by methods described herein. In an embodiment, the macular degeneration is age-related macular degeneration. In a particular embodiment, the age-related macular degeneration is dry age-related macular degeneration.

It will be appreciated that the above embodiments may be combined with one or more, or all, of the additional embodiments described. In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Figure 1:
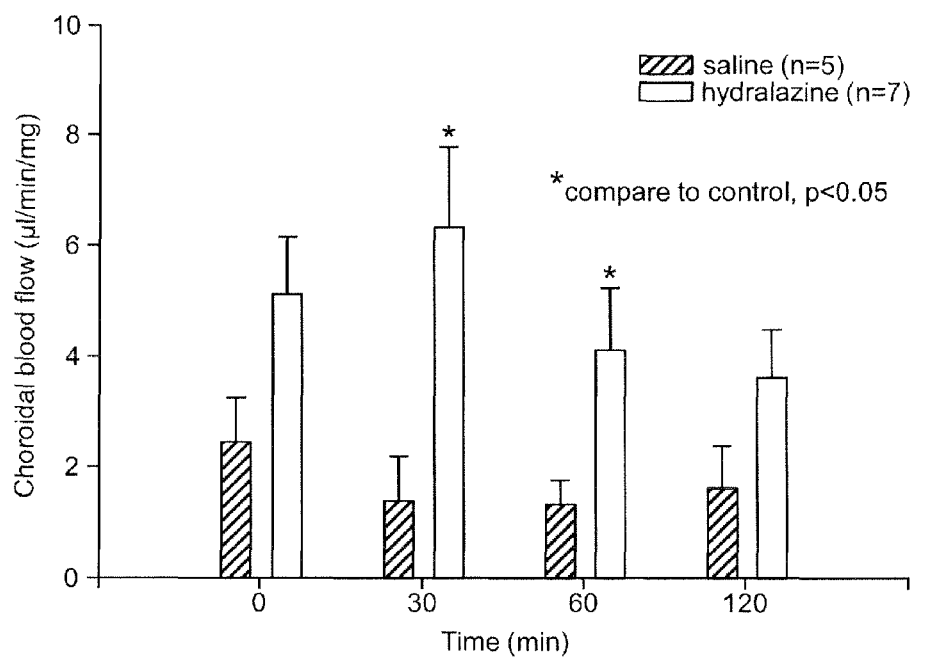
FIG. 1 is a graph of choroidal blood flow in μl/min/mg at 0, 30, 60, and 120 minutes after instillation of a 1% hydralazine hydrochloride formulation.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "drug" includes a single drug as well as two or more of the same or different drugs, reference to an "excipient" includes a single excipient as well as two or more of the same or different excipients, and the like.

Concentrations, amounts, pH values, etc., are often presented herein in a range format. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as a pH of 3.8 to 4.4 should be considered to have specifically disclosed subranges such as 3.8 to 4.4, 3.8 to 4.2, 3.8 to 4.0, 4.0 to 4.4, 4.2 to 4.4, 3.9 to 4.2, 4.0 to 4.2, etc., as well as individual numbers within that range, such as, 3.8, 3.9, 4.0, 4.1, 4.2, 4.3, and 4.4. This construction applies regardless of the breadth of the range and in all contexts throughout this disclosure.

"Therapeutically effective amount" refers to an amount of a pharmaceutically active substance, agent or drug useful in the prevention, treatment, or slowing progression of a visual disorder or visual deterioration or eye disease.

Reference herein to "drug" or "agent" or to any specific composition or compound by name, such as hydralazine, includes the pharmacologically active compound as well as its pharmaceutically acceptable salt, a prodrug such as an ester or an ether, or a salt of a prodrug, or a solvate such as ethanolate, or other derivative of the pharmacologically active compound. Reference to herein to "drug or a salt thereof" or "agent or a salt thereof" or to any specific compound or composition by name, such as hydralazine, in conjunction with "or a salt thereof" intends the pharmacologically active agent and any pharmaceutically acceptable salt of the drug. Salts of the pharmacologically active drugs may be derived from inorganic or organic acids and bases. Examples of inorganic acids include, but are not limited to, hydrochloric, hydrobromic, sulfuric, nitric, perchloric, and phosphoric acids. Examples of bases include, but are not limited to, alkali metal (e.g., sodium) hydroxides, alkaline earth metal (e.g., magnesium) hydroxides, ammonia, and compounds of formula $N-W_4^+$, wherein W is $C_{1-4}$ alkyl. Examples of organic salts include: acetate, propionate, butyrate, hexanoate, heptanoate, undecanoate, palmoate, cyclopentanepropionate, adipate, alginate, aspartate, benzoate, citrate, oxalate, succinate, tartarate, lactate, maleate, fumarate, camphorate, nicotinate, pectinate, picrate, pivalate, tosylate, gluconate, digluconate, hemisulfate, methanesulfonate, ethanesulfonate, 2-hydroxyethanesulfonate, dodecylsulfate, camphorsulfonate, benzenesulfonate, 2-naphthalenesulfonate, thiocyanate, phosphate, glycerophosphate, and phenylpropionate.

Other salts are listed in Remington: The Science and Practice of Pharmacy, 19th Ed., Mack Publishing Co., Easton, Pa. (1995), Chapter 83 (hereinafter REMINGTON).

As used herein an "eye disease" means any variety of diseases, impairments, or defects that cause, vision loss, blurred or decreased central close-up and distance vision, blind spots, objects to appear a different color or shape, neuro-ophthalmic manifestations of vascular eye diseases, including ischemic optic neuropathy, anterior ischemic optic neuropathy, retinal artery occlusion, asymptomatic retinal emboli, asymptomatic retinal embolus or ischemia of retinal tissue, retinal edema, amaurosis fugax, reduction in visual field, occlusion of ocular vessels, stagnation of blood flow within the arteriole, cataracts, glaucoma, proptosis, eyelid retraction, restrictive myopathy, diplopia (double vision), compressive optic neuropathy, and/or exposure keratopathy. In one embodiment, the eye disease is macular degeneration or a diabetic eye disease. In a further embodiment, the eye disease is age-related macular degeneration. In yet a further embodiment, the eye disease is dry or non-neovascular age-related macular degeneration. In another embodiment, the eye disease is diabetic macular edema. It will be appreciated that "eye disease" may encompass one or more eye diseases. That is, the present formulations may treat, prevent, and/or slow/halt the progression of one or more eye diseases. It is not intended that the present invention be limited to treating any particular underlying disease resulting in vision defects or impairments.

As used herein, "macular degeneration" means any condition that causes part of the macula to deteriorate. This degeneration may be partial or total, and it is not intended to be limited to advance stages of the disease. For example, with reference to age-related macular degeneration, "macular degeneration" is intended to include a subject that is diagnosed with drusen even though the subject does not have any symptoms of impaired vision. In non-limiting embodiments, macular degeneration may refer to age-related macular degeneration.

As used herein, a compound "functioning to decrease choroidal neovascularization" means that a statistically significant reduction of choroidal neovascularization, that is measured by methods known in the art, e.g. by fluorescein angiography, after some period of time of administering a compound after physical disruption of the eye's Bruch's membrane, e.g., via a laser or from the eye disease. Detailed descriptions of methods for identifying compounds functioning to decrease choroidal neovascularization are described herein.

"Isomers" means any of two or more substances that are composed of the same elements in the same proportions but differ in the three dimensional arrangement of atoms including enantiomeric (i.e., mirror images) and diastereomeric isomers.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula $-NR,R',R''^+Z^-$, wherein R, R', R'' is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Adverse drug reaction" means any response to a drug that is noxious and/or unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity and liver toxicity). Hypersensitivities are immune-mediated adverse reactions (e.g., anaphylaxis, allergy). Drug interactions are effects, typically adverse, arising from interactions with other drugs, foods or disease states (e.g., warfarin and erythromycin, cisapride and grapefruit, loperamide and *Clostridium difficile* colitis). Complications are diseases caused by a drug (e.g., NSAID-induced gastric ulcer, estrogen-induced thrombosis). The adverse drug reaction may be mediated by known or unknown mechanisms (e.g., agranulocytosis associated with chloramphenicol or clozapine). Such adverse drug reaction can be determined by subject observation, assay or animal model as known in the art.

The term "derivative" when used in relation to a chemical compound refers to a similar structure that upon application, e.g., administration to a subject, is capable of providing, directly or indirectly, the function the chemical compound is disclosed to have (albeit the derivative may have increased or decreased function). For example, substituting one atom for another atom in a chemical compound provides a compound of similar structure, e.g., a carbon atom for a nitrogen atom. The compound of similar structure may be capable of similar function, e.g. to decrease choroidal neovascularization. Certain claimed embodiments are intended to encompass minor changes in chemical structure provided that the derivative can treat, prevent, halt or slow the progression of the eye disease.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

As used herein, the terms "prevent" and "preventing" include the prevention of the recurrence, spread or onset of a disease. It is not intended that the present invention be limited to complete prevention. In some embodiments, the onset is delayed, or the severity of the disease is reduced.

"Subject" means any animal, preferably a human patient, livestock, or domestic pet.

As used herein, the terms "treat" and "treating" are not limited to the case where the subject (e.g. patient) is cured and the disease is eradicated. Rather, the present invention also contemplates treatment that merely reduces symptoms, improves vision (to some degree), delays and/or halts disease progression.

As used herein, the term "pharmaceutically acceptable" means approved by a regulatory agency of the Federal or a state government or listed in the U.S. Pharmacopeia or other generally recognized pharmacopeia for use in animals, and more particularly in humans.

II. Pharmaceutical Ophthalmic Formulations

In a first aspect, an ophthalmic composition or formulation is provided. The pharmaceutical formulation comprises a hypotensive agent including, but not limited to, hydralazine or a salt, substituted derivative, or unsubstituted derivative thereof, and specific other components, that collectively provide an advantageous composition, as will now be described.

In studies conducted in support of the claimed compositions and methods, an ophthalmic formulation comprising hydralazine was prepared as described in Example 1. The formulation comprises, in one embodiment, hydralazine and selected excipients that provide improved stability and/or bioavailability.

Hydralazine

Hydralazine is a benzopyridazine derivative previously used as a hypotensive agent. The biochemistry, physiology, metabolism, and excretion of hydralazine in animals and humans have been well studied (Velliquette et al., 2003, J Pharmacol Exp Ther, 307(3):1104-1111; Carmody et al., 2007, Cardiol Rev, 15(1):46-53; Adorisio et al., 2006, Heart Fail Rev, 11(2):109-123; Artman et al., 1984, Circulation, 69(5):949-954; Cameron et al., 1984, 289(6442):410-412; and Perry et al., 1973, Am J Med, 54(1):58-72). Hydralazine is a direct-acting antihypertensive drug that causes relaxation of arteriolar muscle, exerting a peripheral vasodilatory effect, though the mechanism by which it does so is not fully understood (Freemantle et al., 2008, Coch Dat Sys Rev, 2008(2): 1-5; Brunton et al. eds., 2008, Goodman and Gilman's Manual of Pharmacology and Therapeutics, 11$^{th}$ ed., New York; Apresoline® package insert, Ciba-Geigy, 1995). It is proposed that hydralazine alters calcium metabolism and thereby interferes with calcium movements within vascular smooth muscle that cause the initiation or prolongation of the contractile state. The peripheral vasodilatory effect results in several cardiac effects: decreased arterial blood pressure (diastolic more than systolic); decreased peripheral vascular resistance; and increased heart rate, stroke volume, and cardiac output. Hydralazine usually increases renin activity in plasma, likely in response to reflex sympathetic discharge. The drug also has been found to maintain or increase renal and cerebral blood flow. Some of the anticipated potential effects of vasodilators (as a class) in the eye include dilation of the arterioles, which would be expected to improve circulation in the choroid and retina, and relaxation of arterial or arteriolar wall spasms (due to lesions or other contractures in the eye) and avoidance of sclerosis (Laws, 1964, Can Med Assoc J, 91:325-330).

Hydralazine is well absorbed through the gastrointestinal tract, with a systemic bioavailability of 16% in fast acetylators and 35% in slow acetylators (Brunton 2008; Hydralazine hydrochloride USP package insert, Par Pharmaceuticals, 2005). Hydralazine is N-acetylated in the bowel and/or liver. The plasma half-life of hydralazine is 3-7 hours, though its hypotensive effects can endure up to 12 hours (Par 2005). Hydralazine quickly combines with a-keto acids to form hydrazone, and the major metabolite is hydralazine pyruvic acid hydrazone. Since in the acetylated form hydralazine is inactive, rapid acetylators typically require larger doses than slow acetylators, though approximately half of the U.S. population are fast acetylators; rate of acetylation is a factor in bioavailability but not in systemic elimination of the drug due to its high rate of hepatic clearance (systemic clearance is 50 mL/kg/min, which exceeds hepatic blood flow). The peak concentration of orally administered hydralazine in plasma and maximal hypotensive effect occur within 30-120 minutes of administration. Intramuscular injection of hydralazine induced hypoxia-inducible factor-1α (HIF-1α) protein in tissue extracts, which in turn regulates vascular endothelial growth factor (Knowles et al., 2004, Circ Res, 95(2):162-169—suggesting that hydralazine exerts proangiogenic effects and may be beneficial in ischemic heart disease). Reduced blood flow and focal ischemia in the retina have been suggested to be important factors in the progression of AMD (Grunwald 1998, Metelitsina 2006, Spraul et al., 1998, Invest Ophthalmol Vis Sci, 39(11):2201-2202; Pournaras et al., 2006, Invest Ophthalmol V is Sci, 47(4):1581-1586; Feigl et al., 2007a, Clin Exp Optom, 90(4):263-271; Feigl et al., 2007b, Eye, 21(6):689-696).

In one embodiment, the hydralazine for use in the formulation is a hydralazine salt such as hydralazine hydrochloride. Hydralazine hydrochloride is a white to off-white, odorless, crystalline powder having a molecular weight of 196.64 and having the formula $C_8H_8N_4 \cdot HCl$. Hydralazine hydrochloride USP is soluble 1 in 25 of water and 1 in 500 of alcohol. A 2% solution in water has a pH of about 3.5-4.2 and appears to be very stable at a pH of about 3.5-4.5. A pH profile indicates that hydralazine hydrochloride is highly stable near a pH of 3.5 where the drug is in the cationic form. When in the cationic form, the rate constant at 25° C., pH 3.5 is 1.5 years with less than a 10% loss (obtained by extrapolation).

Preferably, the hydralazine formulation is an ocular or ophthalmic solution or formulation comprising hydralazine or a salt, substituted or unsubstituted derivative thereof. In one particular embodiment, the formulation comprises hydralazine hydrochloride. In another embodiment, the formulation comprises an acetate salt of hydralazine. In embodiments, the ocular solution is an aqueous solution.

Excipients

Exemplary excipients included in the formulation include uptake enhancers, thickening agents and stability enhancers, buffers, preservatives, chelating agents, lubricants, isotonicity agents, acids and bases to adjust the pH, and/or diluents.

Suitable buffers are known in the art and include, without limitation, acetate, ascorbate, tris, sodium acetate trihydrate, acetic acid, citrate buffers, borate, carbonate, acetate and/or phosphate. In embodiments, one or more buffers are used. In one non-limiting embodiment, a suitable amount of buffer to maintain the solution or ointment at a physiologically tolerable range is included in the solution or ointment. In non-limiting embodiments, an amount of buffer suitable to maintain a pH of about 3.8-7.5 or 3.8-4.4 is added to the solution or ointment. The pH range of ophthalmic solutions generally ranges from about 3.0-7.7 with the majority of ophthalmic solutions having a pH of about 5-7. In embodiments, the pH of the present formulation is between about 3.0-7.7 or about 5-7. In other embodiments, the ophthalmic solution has a pH of about 3.5-4.5, 3.5-4.2, 3.5-4.0, 3.8-4.4, or 4.0-4.5. It will be appreciated that the buffer used will depend on the pH to be maintained. In other embodiments, a pH adjuster may be used to adjust the pH of the formulation. It will be appreciated that any pH adjuster known in the art and suitable for topical administration to the eye may be used. In non-limiting embodiments, the pH adjuster is selected from sodium hydroxide and/or hydrochloric acid. Exemplary buffers include sodium acetate trihydrate USP and acetic acid USP (2N). A further exemplary buffer is an acetate buffer solution USP comprising sodium acetate trihydrate USP and acetic acid USP.

Any suitable chelating agent is contemplated including, without limitation, edetate disodium dehydrate. Suitable lubricants include, but are not limited to propylene glycol, polyethylene glycol, polyvinyl alcohol, and glycerin. An exemplary chelating agent is edetate disodium dehydrate USP. An exemplary lubricant is propylene glycol USP.

An isotonicity agent is generally an agent or compound that is physiologically tolerated and that imparts a suitable tonicity to a formulation to prevent the net diffusion of water across cell membranes in contact with the formulation. Suitable isotonicity agents include, but are not limited to salts including sodium chloride and sugars such as dextrose and lactose. The osmolality of the eye is about 290 mOsmol/kg. The osmolality range for ophthalmic solutions is generally between about 250-350 mOsmol/kg with the majority falling between about 290-300 mOsmol/kg. In embodiments, the osmolality of the present formulation should be at or near the osmolality of the eye. In particular, non-limiting, embodiments, the osmolality of the present formulations is generally between about 250-350 mOsmol/kg or between about 290-300 mOsmol/kg. In one particular embodiment, the osmolality of the present formulations is about 300 mOsmol/kg. An exemplary isotonicity agent is sodium chloride USP.

In one embodiment, the formulation has a pH of between about 3.5 and 4.5. In one preferred embodiment, the formulation has a pH of between about 3.8 and 4.4. In another embodiment, the formulation has a pH of between about 4.0 and 4.4.

Suitable preservatives are known in the art and include, but are not limited to, benzalkonium chloride, methylparabenen, chlorobutanol, thimerosol, propylparaben, and polyquaterniaum-1. According to the FDA Advisory Review Panel on OTC Ophthalmic Drug Products (Final Report dated December 1979), the maximum concentration for use in ophthalmic formulations for benzalkonium chloride, USP is 0.013% and the maximum concentration for methylparaben, NF is 0.1-0.2%. Benzalkonium chloride USP is most active against bacteria but is considered weaker against pseudomonads and mold. Methylparaben, NF is most active against fungi and Gram positive bacteria but is considered weaker against Gram negative bacteria. Exemplary preservatives include benzalkonium chloride NF and/or methylparaben NF.

Suitable diluents are known in the art and include, but are not limited to, Purified Water USP and Water for Injection. Exemplary diluents include water, especially water for injection USP, and saline.

Suitable viscosity enhancers are known in the art and include, but are not limited to, polyvinyl alcohol, hydroxypropylmethylcellulose, and polyvinylpyrrolidone.

An exemplary hydralazine formulation is presented in Table 1 and an exemplary method of preparing a formulation is set forth in Example 1.

TABLE 1

Hydralazine Formulation

| Ingredient | Function | Amount |
| --- | --- | --- |
| Hydralazine hydrochloride USP | Active Agent | 1.0 % w/w |
| Sodium acetate trihydrate USP | Buffer | 10 % w/w[1] |
| Acetic acid USP (2N) | Buffer | |
| Edetate disodium dehydrate, USP | Chelation Agent | 0.015 % w/w[1] |
| Propylene glycol, USP | Lubricant | 1.00 % w/w[1] |
| Sodium chloride, USP | Isotonicity Agent | 0.50 % w/w[1] |

TABLE 1-continued

Hydralazine Formulation

| Ingredient | Function | Amount |
| --- | --- | --- |
| Benzalkonium chloride 50% solution, NF | Preservative | 0.02 % w/w[1] |
| Methylparabenen, NF | Preservative | 0.03 % w/w[1] |
| Water | Diluent | 88.435 % w/w[1] |

[1]% w/w not including hydralazine

More generally, the formulation includes the active therapeutic agent, hydralazine, and a carrier. The term "carrier" refers to a diluent, adjuvant, excipient, or vehicle with which the active compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carrier can be water, saline including phosphate-buffered saline, aqueous solvents, polyalkylene glycols, petroleum-based jelly, ethyl cellulose, ethyl oleate, carboxymethyl cellulose, polyvinylpyrrolidine, isopropyl myristate, gum acacia, gelatin, starch paste, talc, keratin, colloidal silica, urea, and the like. Water can be the vehicle when the active compound is administered intravenously. Saline solutions and aqueous dextrose and glycerol solutions can also be employed as liquid carriers. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. Further suitable carriers include, but are not limited to, glycine and hyaluronic acid. The present compositions, if desired, can also contain wetting or emulsifying agents, and/or pH buffering agents. In addition, auxiliary, stabilizing, thickening, emulsifying, lubricating and/or coloring agents can be used.

When administered to a subject, the pharmaceutically acceptable vehicles are preferably sterile. Suitable methods of sterilization are known in the art and include, but are not limited to, heat sterilization, chemical sterilization, and/or sterilization by filtration. In another embodiment, one or more of the ingredients may be separately sterilized and the formulation prepared under aseptic conditions.

The present compositions can take the form of solutions, suspensions, emulsion, sustained-release formulations, or any other form suitable for use. In one embodiment, the pharmaceutically acceptable vehicle is an ophthalmic solution, suspension, emulsion, salve or ointment.

Compositions for administration can optionally include a local anesthetic suitable to administer to the eye to ease pain at the site of administration. Generally, the ingredients are supplied either separately or mixed together in a unit dosage form.

III. Method of Preparing Formulations

In one aspect, the formulation may be prepared by step-wise addition of ingredients. In an embodiment, the method comprises first adding an appropriate amount of a buffer solution to an appropriate amount of purified water with mixing. Preferably, the purified water is placed in a suitably sized container to hold the volume of the final formulation. Any suitable method of mixing is acceptable. A preferred method is continuous mixing such as provided by a stir plate and spin bar as well known to those of skill in the art. The buffer solution may be separately prepared or be purchased commercially. In one non-limiting embodiment, the buffer solution is an acetate buffer solution. In one non-limiting embodiment, the acetate buffer solution comprises sodium acetate, acetic acid, and purified water. Such a buffer solution may be purchased or be prepared. The buffer may be selected with the appropriate pH. In an exemplary embodiment, the acetate buffer solution has a pH of about 4.2-4.6. In a particular embodiment, the buffer has a pH of 4.2. As a non-limiting example, an acetate buffer solution may be prepared by adding 1.75 g sodium acetate and 18.6 ml of acetic acid 2N in a 1 L volumetric flask with purified water, qs to 1000 mL. This exemplary buffer solution should have a pH of about 4.2. It will be appreciate that where the buffer solution is prepared rather than purchased, a prior step of preparing the buffer solution will be required.

Second, an appropriate amount of one or more chelating agents, such as edetate disodium dehydrate, is added to the buffered solution while mixing and the resulting solution (A) is mixed until the chelation agent is completely or nearly dissolved. Third, one or more lubricants are added to the A solution while mixing. The resulting solution (B) is mixed until the lubricant(s) are completely or nearly dissolved. Any lubricant suitable for use in an ophthalmic formulation is contemplated. In one non-limiting embodiment, the lubricant is propylene glycol. Fourth, one or more isotonicity agents are added to the B solution while mixing. The resulting (C) solution is mixed until the isotonicity agent(s) are completely or nearly completely dissolved. Fifth, one or more preservatives are added to the C solution while mixing. The resulting (D) solution is mixed until the preservative(s) are completely or nearly completely dissolved. Sixth, one or more therapeutic agents, including but not limited to hydralazine hydrochloride, are added to the D solution while mixing. The resulting (E) solution is mixed until the therapeutic agent(s) are completely or nearly completely dissolved. It will be appreciate that where more than one type of ingredient, e.g. two or more preservatives, are used, the ingredients may be added together or separately. Where the ingredients are added separately, the solution may be mixed completely or nearly completely before the next ingredient is added. Formulation parameters may be measured and the formulation adjusted accordingly. For example, the pH may be measured and adjusted where needed.

Preparation of an exemplary formulation is detailed in Example 2. As evidenced by the data presented in Example 2, the method of preparation yields a surprisingly stable formulation. As seen in Tables 8-10, the 0.5% and 1.0% hydralazine hydrochloride formulations were favorably stable at all three temperatures in the droptainer container. That is, the w/w % of the active agent decreased by considerably less than about 1% for most of the formulations at each of the three temperatures after one and two months of storage. For many of the formulations, the w/w % of the active agent decreased by considerably less than about 0.5% at each of the three temperatures after one and two months of storage. The 0.5% and 1% formulations were very stable after one, two, and three months, especially with storage at 4° C. and 25° C. The 2% formulation was also very stable and was most stable with storage at 25° C. The formulations are also very stable at a pH of about 4.0-6.6, data not shown. 100% of the active agent was recovered after storage of the formulation in a glass vial for storage (one week to one month) at a pH of 4.0-5.5.

Dosing

The amount of the active compound that is effective in the treatment or prevention of age-related macular degeneration can be determined by standard research techniques. For example, the dosage of the active compound which will be effective in the treatment or prevention of age-related macular degeneration can be determined by administering the active compound to an animal in a model such as, e.g., the animal models known to those skilled in the art or other models such as computer models. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

IV. Methods of Treatment

In one aspect, the formulation is useful in the treatment of eye diseases. In some non-limiting embodiments, the formulation is useful for treating, preventing, halting and/or slowing the progression of macular degeneration. In other non-limiting embodiments, the formulation is useful in treating diabetic macular edema.

A. Macular Degeneration

Macular degeneration is caused by the deterioration of the central portion of the retina known as the macula, the area responsible for focusing the central vision in the eye. Macular degeneration is intended to refer both to macular dystrophies affecting individuals under the age of 50 as well as age-related macular degeneration (AMD or ARMD).

Age-related macular degeneration is the leading cause of vision loss in adults over the age of 50 and the third leading overall cause of blindness worldwide (National Eye Institute). AMD may be characterized as a dry (atrophic, non-neovascular, non-exudative) or wet (neovascular, exudative) form.

While the relationship between the cellular and molecular changes responsible for the development and progression of AMD is not clearly understood, the clinical course is better delineated. AMD starts with non-exudative (dry) senescent changes to the supportive retinal pigment epithelium (RPE) and Bruch's membrane underlying the macula. Nonexudative AMD can progress to more severe atrophic AMD (also known as geographic atrophy) and also develop the exudative (wet) form characterized by a pathological choroidal neovascular membrane growing from beneath the macula. Severe vision loss is typically associated with the 10-15% of all patients with AMD that develop the exudative form; however, up to 20% of legal blindness from AMD is due to the advanced atrophic nonexudative form.

The dry form is non-neovascular, accounts for about 90% of AMD cases, and is identified with multiple, small, round, yellow-white spots called drusen. These spots are typically located in the back of the eye at the level of the outer retina. Subjects with these spots may have excellent vision and no symptoms. The drusen may accumulate between the retina and the choroid, which may cause the retina to become detached. Nonexudative AMD has three clinical stages: early, intermediate and late. These stages are characterized clinically by the extent and size of yellow drusen deposits beneath the macula in addition to the degree of abnormalities in the RPE. With early nonexudative AMD, the drusen are small to intermediate in size, and there are minimal to no pigment abnormalities. By the time nonexudative AMD has progressed to geographic atrophy, the clinical findings have passed through the stage of extensive macular drusen and demonstrate localized obliteration of the RPE. If located beneath the central macula (i.e. fovea), the geographic atrophy of the RPE results in the loss of the overlying photoreceptors and functional vision.

In the neovascular, wet form, newly created abnormal blood vessels grow under the center of the retina. These blood vessels leak, bleed, and scar the retina, distorting vision or destroying central vision. Vision distortion may start in one eye and may affect the other eye later. The wet form accounts for 10% of AMD cases, but accounts for 90% of the vision loss caused by AMD. It is estimated that 10% of dry AMD cases progress to wet AMD annually.

Several factors are potentially responsible for the development and progression of AMD. The observation that heart disease and AMD share high blood pressure and subclinical atherosclerosis as risk factors has led to the development of the hemodynamic model (also known as vascular model) of AMD pathogenesis. In a manner homologous to systemic vascular disease, this model contends that AMD is a form of vascular disease in which sclerotic deposits, decreased compliance of ocular tissue, and decreased blood flow through the choroidal vasculature lead to disease progression. In particular, the model asserts that progressive infiltration and deposition of lipids within the macula decreases the compliance of ocular tissues and narrows the macular choriocapillaris. This choriocapillaris narrowing compounds the normal narrowing associated with age and further decreases blood flow with elevated hydrostatic pressure. This, in turn, reduces the clearance of the lipoproteins and other materials secreted by the RPE. The result is clinically apparent drusen and pigmentary changes, as well as calcification and fracture of the Bruch's membrane, which leads to choroidal neovascularization.

There is a growing body of evidence that inflammation also plays a role in AMD. The complement components are the best understood inflammatory mediators in AMD. Complement C5 and membrane attack complexes consisting of complement components 5b-9 have been detected in drusen. Similarly, a variety of studies have demonstrated the presence of immune complexes, complement and/or complement regulatory proteins localized to drusen, RPE cells and/or Bruch's membrane. Additionally, numerous genetic studies support the role of complement in AMD. In addition, tissue-destructive macrophages are thought to exacerbate AMD. Thus, one or more of therapeutically increasing the choroidal blood flow, reducing oxidative stress, and/or controlling chronic inflammation could significantly treat and/or slow the progression of AMD.

One symptom of macular degeneration is a change in central vision. The patient may notice blurred central vision or a blank spot on the page when reading. The patient may notice visual distortion such as bending of straight lines. Images may appear smaller. Some patients notice a change in color perception and some experience abnormal light sensations. These symptoms may come on suddenly and become progressively more troublesome.

As used herein a diagnosis of macular degeneration may entail any analysis of macular changes or function in a subject. It is not intended to be limited to any particular method. For example, an eye examiner, e.g., doctor, may dilate the pupil with eye drops and examine the interior of the eye, looking at the retina for the presence of yellow bumps of drusen, eye lesions, or for gross changes in the macula such as thinning. The eye examiner may also administer a visual field test, looking for blank spots in the central vision. The examiner may call for fluorescein angiography (intravenous injection of fluorescent dye followed by visual examination and photography of the back of the eye) to determine if blood vessels in the retina are leaking.

Some risk factors for having macular degeneration include age, smoking, and a diet that is rich in saturated fat. Others may be at risk for macular degeneration because of genetic heritage or environmental exposure.

In embodiments, the methods described herein relate to treatment or prevention of age-related macular degeneration, preferably prophylactic prevention and treatment. In other embodiments, the methods described herein relate to preventing or slowing the progression of age-related macular degeneration with the formulations described herein. In one embodiment, a method of preventing or slowing CNV in a patient diagnosed with non-exudative or exudative AMD with the formulations described herein is contemplated.

In one embodiment, a 1% (w/w) hydralazine ophthalmic solution is instilled in one or more affected eye at least once daily, and in other embodiments, between one to five times daily. In other embodiments, a 0.5%-4% w/w hydralazine ophthalmic solution is instilled in one or more affected eye at least once daily, and in other embodiments, one to five times daily. In yet further embodiments, a 0.5%-2% w/w hydralazine ophthalmic solution is instilled in one or more affected eye at least once daily, and in other embodiments, one to five times daily. In one particular embodiment, 1% w/w hydralazine ophthalmic solution is instilled in one or more affected eye at least once daily, and in other embodiments, one or three times daily.

As seen from the safety data as shown in Example 3, a hydralazine hydrochloride ophthalmic solution, prepared according to the methods described herein, was safe and generally well tolerated in humans, with a low incidence of treatment-emergent Adverse Events (AE) that were generally mild in severity and relatively evenly distributed among the two subject populations. There were no Significant Adverse Events (SAE), no deaths, and no other clinically significant safety findings during the course of the study. Ocular hyperemia was the most commonly reported treatment related ocular AE, reported by most subjects in this study. The incidence of ocular hyperemia was consistent with the peripheral vasodilatory effects of hydralazine and was not unexpected. Thus, repeated doses of a topical hydralazine hydrochloride formulation were safe and well tolerated in humans (Ralston et al., 2010, ARVO Abstracts, Abstract No. 913/A196).

Examples 4 and 5 set forth single dose and repeat dose studies using the formulation described herein prepared in accord to the method described herein. In Example 5, a 28-day, GLP-compliant, repeat dose ocular study using the rabbit model shows that ocular irritation occurring at initial dosing becomes well tolerated during repeat dosing. The lack of any significant dose-related toxicity further indicates a reasonable potential for safety with concentrations of hydralazine hydrochloride at least up to 2.0% w/w in this particularly sensitive animal model.

Figure 2:
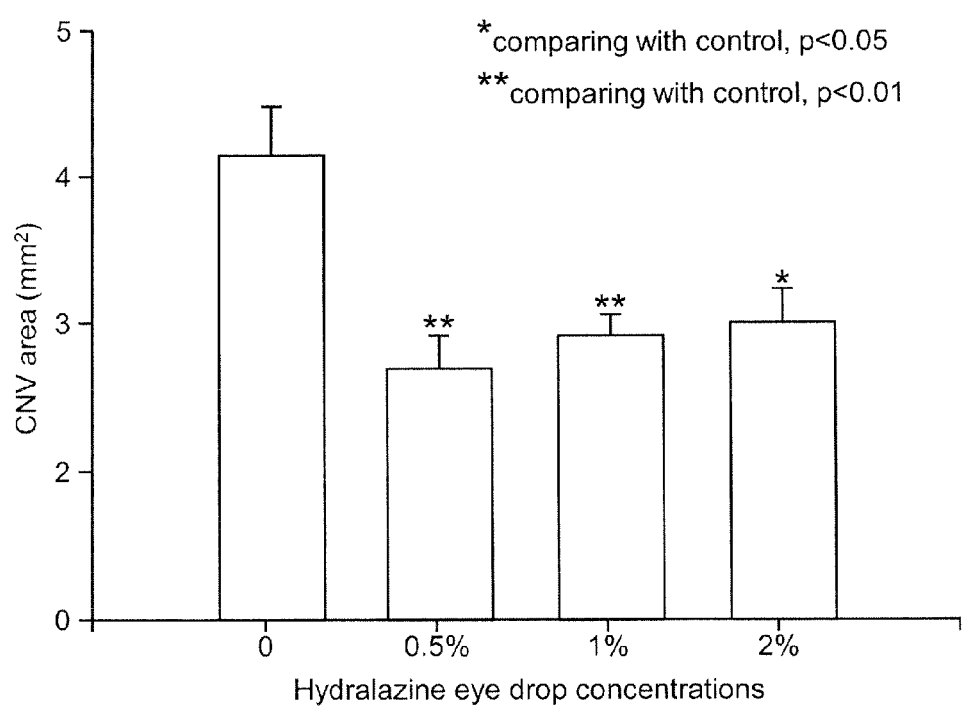
FIG. 2 is a graph of CNV area in $mm^2$ after administration of 0%, 0.5%, 1%, and 2% hydralazine hydrochloride formulations as measured by fluorescein.
Figure 3:
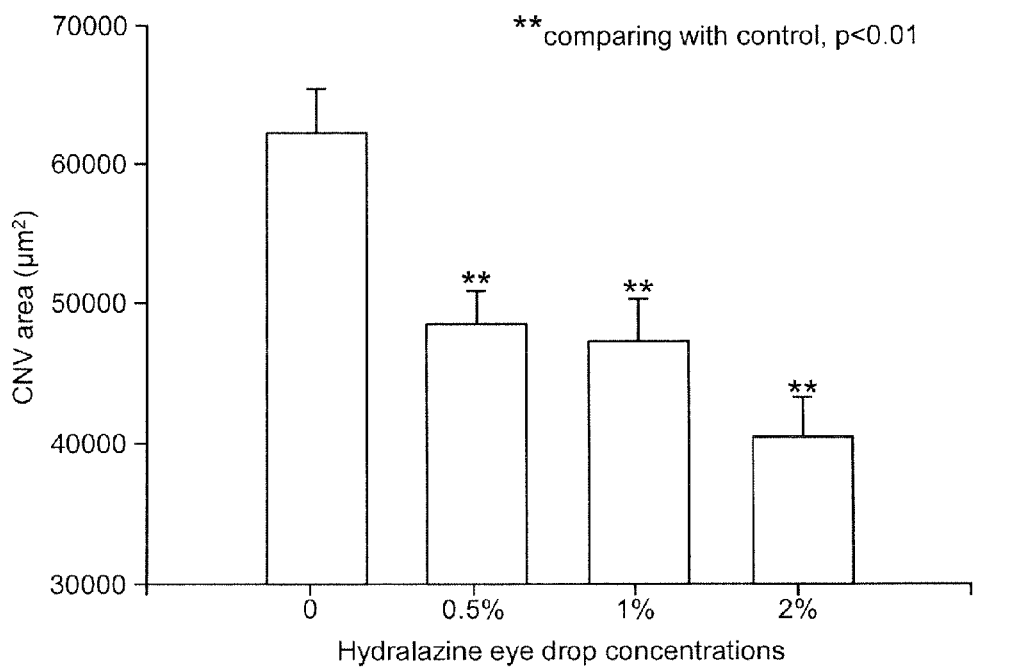
FIG. 3 is a graph of CNV area in $\mu m^2$ after administration of 0%, 0.5%, 1%, and 2% hydralazine hydrochloride formulations as measured by choroidal flat mount.

It has been proposed that reduced choroidal blood flow and focal ischemia may be a causative factor in the progression of events leading to early AMD (Feigl et al. 2007b). Further, the long-term effects of hypoxia in the choroid and retina have been proposed to be responsible for upregulation of endothelial growth factors and the development of the choroidal neovascular growth that is characteristic of the progression from early to late stage AMD (Feigl et al. 2007b). As shown in Example 6, instillation of hydralazine 1.0% eyedrops improved the choroidal blood flow significantly in the rabbit eye model. As seen in FIG. 1, 30 minutes after instillation with 1% hydralazine formulation choroidal blood flow was not only maintained from the starting point, but actually improved. In contrast, instillation with the control resulted in a decrease in choroidal blood flow (by about 40% looking at FIG. 1). After 30 minutes, treatment with the 1% hydralazine formulation resulted in a choroidal blood flow that was at least about 75% higher, or at least about three to four times higher, than the control. In contrast, treatment with the control resulted in a decrease in choroidal blood flow by about 40%. As also seen in FIG. 1, 60 minutes after instillation with the hydralazine formulation, choroidal blood flow was at least about 65% higher, or at least about two to three times higher, than the control. After 120 minutes, treatment with the 1% hydralazine formulation resulted in a choroidal blood flow that was at least about 50% higher, or at least about two times higher, than the control. In contrast, treatment with the control resulted in a decrease in choroidal blood flow by about 30%. An increase in choroidal blood flow, as compared to the control, was maintained for at least 2 hours. In the laser-induced CNV model, installation of hydralazine eyedrops (at all concentrations) for 4 weeks reduced the area of CNV formation significantly, see Example 7. The effect of hydralazine formulations (0%, 0.5%, 1%, and 2%. w/w) on CNV formation are shown in FIGS. 2 and 3 (as measured by fluorescein or y choroidal flat mount respectively). As seen in FIG. 2, each of the hydralazine formulations reduced CNV area as measured by fluorescein. The 0.5% formulation reduced CNV area by about 33%. The 1% formulation reduced CNV area by about 30% while the 2% formulation reduced CNV area by about 26%. As seen in FIG. 3, each of the hydralazine formulations reduced CNV area as measured by choroidal flat mount. The 0.5% formulation reduced CNV area by about 20-25%. The 1% formulation reduced CNV area by about 25% while the 2% formulation reduced CNV area by about 30-35%. Further, as described in Example 8, tube formation by HUVEC in vitro was prevented by hydralazine, which can be taken as a sign of anti-neovascularization activity. These data suggest that hydralazine may have multiple mechanisms of action and could reduce the extent of CNV formation through both the improvement of choroidal blood flow and the prevention of new vessel formation.

The selective toxicity of sodium iodate on cells in the RPE has been known for many years (Noell, 1953, Am J Ophthalmol, 36(6:2):103-116). Damage to and dysfunction of the RPE is thought to be one of the early events in the progression of AMD. Accordingly, this approach of creating chemically induced damage selectively in the RPE layer of the retina has been used to investigate potential therapies for AMD (Li, et al., 2006, Invest Ophthalmol Vis Sci, 47(4):1646-1652; Obata et al., 2005, Eye, 19(4):464-468). As shown in Examples 9 and 10, high concentrations of $NaIO_3$ are toxic to human RPE cells in vitro. Consistent with literature reports, a single intravenous injection of $NaIO_3$ caused significant damage to the retina of rats in a time- and dose-dependent fashion. High doses of $NaIO_3$ caused damage throughout the retina as demonstrated by histopathology and the suppression of electrophysiological signals originating from the photoreceptor cells (a-wave), the neural retina (b-wave), and the RPE cells (c-wave). By adjusting the injected dose of $NaIO_3$, conditions were identified in the rat in which the damage appears to be restricted to the RPE cells. The ERG c-wave signal was suppressed, but the a-wave and b-wave signals remained at normal levels. The $NaIO_3$-induced selective suppression of the c-wave signal persisted for more than 4 weeks. Thus, these parameters may be useful as a rat model for nonexudative AMD.

Figure 4:
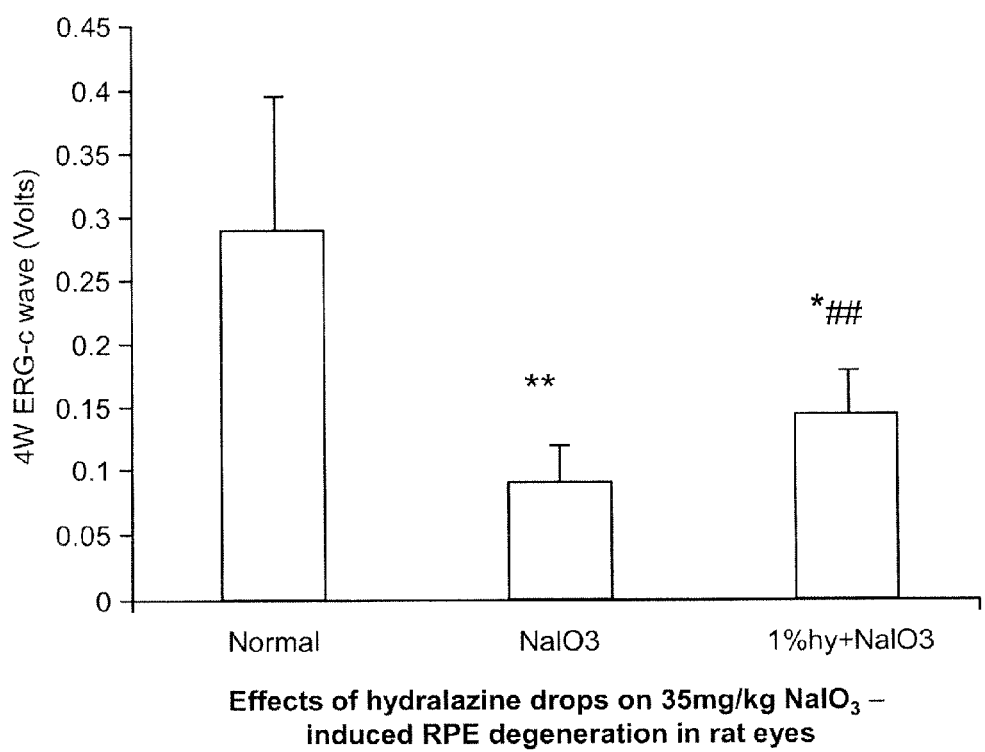
FIG. 4 is a graph of the ERG c-wave signal in Volts to show the effect of a 1.0% hydralazine hydrochloride formulation on $NaIO_3$-induced RPE degeneration in the rat retina (mean±standard deviation: **=P<0.01 or *##=P<0.01).

Using these optimized conditions (35 mg/kg $NaIO_3$ and 4 weeks post injection) in this model, it has been demonstrated that instillation of hydralazine 1.0% ophthalmic solution 3 times daily for the 4 week duration of the experiment significantly decreased the electrophysiological deficit observed in the ERG c-wave signal created by injection of $NaIO_3$ (Example 10). As seen in FIG. 4, instillation of $NaIO_3$ resulted in a 70% decrease in ERG c-wave as compared to the control. Installation of the 1% hydralazine formulation resulted in only about 50% decrease in the ERC c-wave signal. Thus, instillation of the 1% hydralazine formulation maintained about 20% of the ERG c-wave signal as compared to $NaIO_3$ injection alone. The data described in Example 10 also demonstrates that topical installation delivers sufficient hydralazine to the retina to exert the protective effect. The mechanism(s) by which hydralazine protects the RPE from $NaIO_3$-induced damage may be related to the drug's ability to increase choroidal blood flow or to its antioxidant properties. By increasing blood and oxygen flow to the retina, hydralazine might postpone the development of nonexudative age-related macular degeneration and may be used as a treatment for early stage (dry) AMD. In an embodiment, the formulations described herein are useful in a method of increasing choroidal blood flow in a patient diagnosed with non-exudative or exudative AMD.

The results of the $NaIO_3$ induced dry AMD model in rats as described in Examples 9 and 10 demonstrate the ability of a hydralazine hydrochloride formulation to protect retinal pigment epithelium (RPE) cells from damage induced by exposure to $NaIO_3$ and thus protect and possibly restore visual function in patients with dry AMD.

It has been proposed that the loss of RPE cells is a primary manifestation of the early phase of AMD (Cai et al., Prog Retin Eye Res, 2000, 19(2):205-221). Oxidative stress may play a role in the loss of the RPE cells and the pathogenesis of AMD (Beatty et al., 2000, Surv Ophthalmol, 45(2):115-134; Finkel et al., 2000, Nature, 408(6809):239-247). An increase in oxidative stress due to a reduction in the existing protective mechanisms or to an increase in the number and concentration of reactive oxygen species (ROS) are believed to contribute in part to the pathogenesis of AMD (Boulton et al., 1994, Br J Ophthalmol, 78(2):125-129). Hydralazine has antioxidant and vasodilatory properties which may be useful in the treatment of AMD.

It has further been reported that hypoxia can cause death of RPE cells through an oxidative stress-induced mechanism (Cai 2000). There are several effects linked to hypoxia and oxidative injury (Emerit et al., 1998, Handbook of Free Radical and Antioxidants in Biomedicine, Quintanilha eds., CRC Press), including uncoupling of mitochondrial oxidative phosphorylation and degradation of adenosine triphosphate to adenosine diphosphate. Moreover, the sudden decrease in $O_2$ tension allows the release of free radicals from the tightly controlled electron transport chain, and the reactions of these ROS with neighboring membrane lipids result in membrane and cell damage. In order to evaluate the ability of hydralazine to protect cells against hypoxia-induced damage, ARPE-19 cells were incubated with various concentrations of hydralazine for 24-72 hours while exposed to a hypoxic environment (1% $O_2$) in a hypoxia controlling chamber. 1 µg/mL of the hydralazine formulation significantly reduced hypoxia-induced damage to the ARPE-19 cells at 48 hours and 72 hours. This data indicates that hydralazine can prevent hypoxia-induced cell damage but not the chemical ($NaN_3$)-induced cell damage intended to chemically mimic hypoxia. Without being limited as to theory, this difference may be due to the different mechanisms of cell injury caused by the chemical agent $NaN_3$ and the ROS released from mitochondria under conditions of hypoxia.

As described in Example 11, human retinal pigment epithelium cells (ARPE-19 cells) were used in vitro to investigate the antioxidant properties of hydralazine and to evaluate the ability of hydralazine to protect cells from ROS-related damage or hypoxia-related damage.

A free radical is a molecule with an odd, unpaired electron; this unpaired electron makes the molecule unstable and highly reactive (Fantone et al. 1985, Hum Pathol, 16(10):973-978; Thompson et al., 1986, Prog Cardiovasc Dis, 28(6):449-462; McCord et al., 1985, N Engl J Med, 312(3):159-163). Oxygen free radicals, the superoxide anion ($O_2$—), the hydroxyl radical (OH—), and their intermediary, hydrogen peroxide ($H_2O_2$), are believed to be generated in tissue during ischemia and at the time of reperfusion. These ROS can be cytotoxic to cells through a wide variety of pathways including: reaction with fatty acids, which leads to the formation of lipid peroxides in membranes; oxidation of amino acids in proteins; oxidation of sulfhydryl groups; and polypeptide chain scission (Thompson 1986, McCord 1985, Kloner et al., 1989, Circulation, 80(5):1115-1127).

Tert-Butyl hydroperoxide (t-BHP), an organic hydroperoxide (Rush et al., 1985, Toxicol Appl Pharmacol, 78(3):473-483), can be metabolized in the hepatocyte by glutathione peroxidase, generating oxidized glutathione (Alia et al., 2006, Toxicol Appl Pharmacol, 212(2):110-118). Depletion of glutathione (GSH) and nicotinamide adenine dinucleotide phosphate oxidation are associated with altered calcium homeostasis, leading to loss of cell viability (Martin et al., 2001, Biochem Pharmacol, 62(6):705-712). Alternatively, t-BHP can be converted into its peroxyl and alkoxyl free radicals by cytochrome P450 enzymes and by free iron dependent reactions. These free radicals can subsequently initiate lipid peroxidation, forming covalent bonds with cellular molecules (such as DNA and proteins) and further decrease GSH levels. The latter effect, in addition to altering calcium homeostasis, affects mitochondrial membrane potential, eventually causing cell death (Van der Zee et al., 1996, Free Radic Biol Med, 20(2):199-206; Hix et al., 2000, Chem Res Toxicol, 13(10):1056-1064). It is obvious that ROS (Martin 2001; Lima et al., 2006, Life Sci, 79(21):2056-2068), t-BHP radicals (Van der Zee 1996; Davies, 1989, Biochem J, 257(2):603-606) and intracellular iron ions (Hix 2000) are involved in the toxicity of t-BHP; direct effects on these parameters would tend to reduce the level of damage. $H_2O_2$ can form highly reactive hydroxyl radicals (.OH) by Fenton reaction with intracellular iron that are capable of degrading most organic materials (Pesakhov et al., 2007, Biochim Biophys Acta, 1768(3):590-597). According to the data shown in Example 11, hydralazine is able to protect cells against t-BHP and $H_2O_2$ induced cytotoxicity.

As described in Example 11 and herein, three oxidative stress-inducing agents ($H_2O_2$, t-BHP, and $NaN_3$) were used to evaluate the ability of hydralazine to protect ARPE-19 cells against ROS-induced damage and against hypoxia-induced damage. The data showed that the hydralazine formulation inhibited t-BHP and $H_2O_2$ induced oxidative stress damage in a concentration dependent manner but had little or no effect on the damage caused by $NaN_3$.

The hydralazine formulation demonstrated statistically significant inhibition of tBHP-induced cell damage in an apparent concentration-dependent manner after insult with 0.01 mM and 0.03 mM of tBHP. The maximum viability protection effect after insult with both 0.01 and 0.03 mM tBHP was observed with 100 µg/mL of hydralazine.

The hydralazine formulation demonstrated statistically significant inhibition of $H_2O_2$-induced cell damage in an apparent concentration-dependent manner after insult with 0.3 mM and 1.0 mM of $H_2O_2$. The maximum viability protection effect after insult with 0.3 mM $H_2O_2$ was observed with 30 µg/mL of hydralazine, and after 0.3 mM $H_2O_2$, with 30 µg/mL of hydralazine. The maximum reversion effects were seen with 1 µg/mL of hydralazine at 48 hours and 72 hours.

Mitochondrial toxins could offer an alternative to glutamate intoxication (intoxication caused by glutamine, which is an excitatory agent to induce calcium flooding in the intracellular site to kill the cells) to modify the reversible energy failure that occurs during transient ischemia in vivo. Sodium azide ($NaN_3$) has already been used to induce "chemical ischemia" in cell cultures (Varming et al., 1996, J Neurosci Res, 44(1):40-46; Grammatopoulos et al., 2004, Neurosci Res, 50(3):299-306; Grammatopoulos et al., 2002, Brain Res Mol Brain Res, 99(2):114-124) as well as in in-vivo experiments (Vecsei et al., 2001, J Neural Transm, 108(3): 273-278). Its precise mechanism of action remains partially obscure. The effects are usually attributed to cytochrome c oxidase-respiratory chain complex IV-inhibition, and superoxide might be the major product released from the mitochondria after blockage of the electron transfer chain (Duranteau et al., 1998, J Biol Chem, 273(19):11619-11624). In other experiments, not shown, ARPE-19 cells were exposed to $NaN_3$ alone or in the presence of hydralazine (at concentrations of 1, 3, 10, 30, 100 µg/mL). The proportion of viable ARPE cells after insult with $NaN_3$ (0.1-100 mM) and treatment with hydralazine was measured by MTT assay and no significant effect on $NaN_3$ chemically-induced hypoxia was seen in hydralazine-treated ARPE-19 cells. In these experiments, hydralazine did not reverse $NaN_3$— induced cytotoxicity, which may indicate that hydralazine will not antagonize mitochondria-derived ROS.

Thus, hydralazine formulations afford significant protection against hypoxia-induced damage to ARPE-19 cells in vitro. Without being limited as to theory, the effect may be due to a free radical scavenge action of hydralazine to quench the ROS. Although the intracellular signaling involved in oxidative stress-mediated damage to RPE cells is still poorly understood, identification of the chemicals involved in either antioxidant defense or mediation of the oxidative stress response in RPE cells should allow the future development of therapeutic strategies against AMD. Hydralazine has the potential to protect the RPE cells against damage caused by hypoxia and ROS and therefore treat age-related macular degeneration (AMD) and ischemic retinopathy.

The ocular and systemic safety profile of hydralazine has been well established and is well understood based on the previous nonclinical and clinical studies and the history of systemic use for over 50 years. This data is supported by the results of the Example 6 for treatment of dry AMD with a hydralazine hydrochloride ophthalmic solution.

B. Diabetic Macular Edema or Diabetic Macular Degeneration

In another non-limiting embodiment, the formulations disclosed herein are useful in treating or preventing diabetic macular edema or diabetic macular degeneration. Diabetic macular degeneration is the deterioration of the macula due to diabetes. Cystoid macular degeneration is the loss of vision in the macula due to fluid-filled areas (cysts) in the macular region. This may be a result of other disorders, inflammation, or high myopia.

EXAMPLES

The following examples are illustrative in nature and are in no way intended to be limiting.

Example 1

Hydralazine Formulation

A formulation for use as a hydralazine ophthalmic solution was prepared. 5306 g of purified water, USP was added to a 6 L flask with a spin bar with mixing. 600 g of a Acetate Buffer Solution (pH 4.2), comprising sodium acetate and acetic acid (2N), was added to the purified water in the 6 L flask while stirring. Mixing was continued until uniformity was reached. 0.9 g of edetate disodium, USP was added to the flask and mixed until dissolved. Next, 60 g of propylene glycol, USP was added to the flask and mixed until dissolved. Next, 30 g of sodium chloride, USP was added to the flask and mixed until dissolved. 1.2 g of benzalkonium chloride 50% solution, NF was added to the flask and mixed until uniform. Finally, 1.8 g of methylparaben, NF was added to the flask and mixed until dissolved. The pH of the resulting solution was 4.4.

To prepare the hydralazine formulation, an amount of hydralazine hydrochloride was then added to the solution and mixed until uniform.

Example 2

Storage Stability of Hydralazine Formulation 0.5%, 1%, and 2% hydralazine hydrochloride formulations were prepared essentially as described in Example 1 to assess the stability of the formulations. The ingredients and percentages of the formulations are given in Table 3 below.

TABLE 3

Formulation Summary

| Ingredient | CAS# | 0.5% Formulation (w/w %) | 1.0% Formulation (w/w %) | 2.0% Formulation (w/w %) | Control (w/w %) |
|---|---|---|---|---|---|
| Purified Water, USP | 7732-18-5 | 88.045 | 87.615 | 86.775 | 88.435 |
| Acetate Buffer Solution 4.2 USP | 6161-90-4 7732-18-5 64-19-7 | 10.00 | 10.00 | 10.00 | 10.00 |
| Edetate Disodium, USP | 6381-92-6 | 0.015 | 0.015 | 0.015 | 0.015 |
| Propylene Glycol, USP | 57-55-6 | 1.00 | 1.00 | 1.00 | 1.00 |
| Sodium Chloride, USP | 7647-14-5 | 0.35 | 0.24 | 0 | 0.50 |
| Benzalkonium Chloride, 50%, Solution, NF | 8001-54-5 7732-18-5 64-17-5 | 0.02 | 0.02 | 0.02 | 0.02 |
| Methylparaben, NF | 99-76-3 | 0.03 | 0.03 | 0.03 | 0.03 |
| Hydralazine Hydrochloride, USP | 304-20-1 | 0.54* | 1.08* | 2.16* | 0 |

*Allowing for 8% overage for manufacturing losses and raw material purity.

The control formulation was placed in an 8 mL E-C amber glass sample vials with a rubber lined cap (Item 224735, Lot 1402565, Wheaton, Millville, N.J.). The hydralazine hydrochloride formulations were placed in 6 cc cylinder LDPE round with bead droptainers with a 13 mm LDPE controlled drop tip, 40 µL and a 13 mm-425 polypropylene finish closure (Comar Packaging, Buena, N.J.). The formulations were stored for three months at 4° C.±2° C., 25° C.±2° C., and 40° C.±2° C. to assess storage at room temperature, with refrigeration, and accelerated. The pH, osmolality and w/w % of active ingredient was tested at time zero with the results shown in Table 4 below. The pH, appearance, and w/w % of the active ingredient were tested after one month, after two months, and after three months with the results shown in Tables 5-13 below.

The Amber glass vial testing of the control was discontinued after one month due to the pH drift and decrease in assay results (results not shown). The shift in pH is suspected to be due to the alkalinity of the glass vials.

TABLE 4

Initial Formulation Measurements

| wt % Hydralazine hydrochloride | pH | Osmolality (mOsmol/Kg) | Assay |
|---|---|---|---|
| 0.0 | 4.3 | 313 | 0 |
| 0.5 | 4.4 | 312 | 0.540 |

TABLE 4-continued

Initial Formulation Measurements

| wt % Hydralazine hydrochloride | pH | Osmolality (mOsmol/Kg) | Assay |
|---|---|---|---|
| 1.0 | 4.3 | 316 | 1.083 |
| 2.0 | 4.4 | 318 | 2.180 |

TABLE 5

Formulation Measurements After One Month Storage at 4° C. ± 2° C.

| wt % Hydralazine hydrochloride | pH | Description | Assay |
|---|---|---|---|
| 0.5 | 4.3 | Pass | 0.539 |
| 1.0 | 4.1 | Pass | 1.076 |
| 2.0 | 4.3 | Large crystal formations | 2.162 |

TABLE 6

Formulation Measurements After One Month Storage at 25° C. ± 2° C.

| wt % Hydralazine hydrochloride | pH | Description | Assay |
|---|---|---|---|
| 0.5 | 4.3 | Pass | 0.538 |
| 1.0 | 4.1 | Pass | 1.080 |
| 2.0 | 4.3 | Pass | 2.171 |

TABLE 7

Formulation Measurements After One Month Storage at 40° C. ± 2° C.

| wt % Hydralazine hydrochloride | pH | Description | Assay |
|---|---|---|---|
| 0.5 | 4.3 | Pass | 0.536 |
| 1.0 | 4.1 | Pass | 1.074 |
| 2.0 | 4.2 | Slightly darkened | 2.157 |

TABLE 8

Formulation Measurements After Two Months Storage at 4° C. ± 2° C.

| wt % Hydralazine hydrochloride | pH | Description | Assay |
|---|---|---|---|
| 0.5 | 4.2 | Pass | 0.5374 |
| 1.0 | 4.0 | Pass | 1.0843 |
| 2.0 | 4.2 | Large crystal formations | 2.1755 |

TABLE 9

Formulation Measurements After Two Months Storage at 25° C. ± 2° C.

| wt % Hydralazine hydrochloride | pH | Description | Assay |
|---|---|---|---|
| 0.5 | 4.2 | Pass | 0.5364 |
| 1.0 | 4.0 | Pass | 1.0788 |
| 2.0 | 4.1 | Pass | 2.1757 |

TABLE 10

Formulation Measurements After Two Months Storage at 40° C. ± 2° C.

| wt % Hydralazine hydrochloride | pH | Description | Assay |
|---|---|---|---|
| 0.5 | 4.1 | Pass | 0.5338 |
| 1.0 | 3.9 | Pass | 1.0795 |
| 2.0 | 4.0 | Slightly darkened | 2.1480 |

TABLE 11

Formulation Measurements After Three Months Storage at 4° C. ± 2° C.

| wt % Hydralazine hydrochloride | pH | Description | Assay |
|---|---|---|---|
| 0.5 | 4.3 | Pass | 0.5361 |
| 1.0 | 4.1 | Pass | 1.0734 |
| 2.0 | 4.3 | Large crystal formations | 2.0895 |

TABLE 12

Formulation Measurements After Three Months Storage at 25° C. ± 2° C.

| wt % Hydralazine hydrochloride | pH | Description | Assay |
|---|---|---|---|
| 0.5 | 4.3 | Pass | 0.5367 |
| 1.0 | 4.1 | Pass | 1.0786 |
| 2.0 | 4.2 | Slightly darkened | 2.1639 |

TABLE 13

Formulation Measurements After Three Months Storage at 40° C. ± 2° C.

| wt % Hydralazine hydrochloride | pH | Description | Assay |
|---|---|---|---|
| 0.5 | 4.2 | Pass | 0.5319 |
| 1.0 | 4.0 | Slightly darkened | 1.0628 |
| 2.0 | 3.6 | Extremely dark amber | 1.9718 |

A "pass" for the description of the formulation refers to a clear, colorless solution by visual inspection. pH was measured with the Fischer Scientific Accumet Basic pH meter.

Example 3

Effect on Choroidal Blood Flow after Administration of Hydralazine Formulation

A single center, open-label study in thirty-one (31) patients age 50 years and older: 20 patients were free of any clinically significant ocular diseases or abnormalities and had a Snellen equivalent best-corrected visual acuity (BCVA) better than 20/30 and 11 patients had signs and symptoms of early non-exudative age-related macular degeneration (dry AMD) was conducted. Safety, comfort and choroidal blood flow was evaluated after seven topical ocular administrations of a hydralazine hydrochloride formulation over a 3 day period.

Subjects in the dry AMD group had evidence of small and intermediate drusen, minimal or no pigment abnormalities in the macula (i.e., risk factor 2 on the AREDS Simplified Grading Scale), and a Snellen equivalent best corrected visual acuity (BCVA) equal to or better than 20/100. All subjects had sufficiently clear ocular media to permit accurate measurement of choroidal blood flow. This study revealed transiently increased conjunctival hyperemia but no other safety or tolerability concerns.

The patients received 1 drop of test material in one eye and vehicle control in the contra-lateral eye. The patients administered the first dose of each day in the clinical setting and self-administered the remaining two doses of the day at prescribed time points. The following parameters were assessed:

Visual acuity (Snellen)
Intraocular pressure
Complete anterior segment slit-lamp examination
Dilated posterior segment slit-lamp examination
Collection of AEs (elicited and observed)
Vital signs
Choroidal blood flow assessed using a compact laser Doppler flowmeter provided by Gevaltec AG (Switzerland).

A primary objective of the study was to evaluate the safety and comfort of a hydralazine hydrochloride ophthalmic solution, prepared as set forth in Example 1. However, in order to obtain early clinical pharmacological data on hydralazine hydrochloride ophthalmic formulation activity, the effects of test material on patients' choroidal blood flow was also evaluated. Prior to administration of the first dose on each day, patients were assessed for visual acuity by Snellen eye chart, vital signs, intra-ocular pressure (IOP), general eye health by biomicroscopy and choroidal blood flow. After administration of the first dose on each day, patients were monitored over a 1 or 4 hour time period for comfort, choroidal blood flow, IOP and general eye health. On day one, the evaluations were after 30, 60, 120, and 240 minutes post hydralazine hydrochloride administration. On days 2 and 3, the evaluations were after the first two time-points. The 7th dose was administered in the morning on day 3. Seven days after the final dose, patients were contacted via telephone to evaluate any post study adverse events or issues.

Choroidal Blood Flow

No clinically significant changes from baseline were found in either eye for intra-ocular pressure (IOP), visual acuity (VA), anterior- and posterior-segment biomicroscopy findings, and vital signs. No other safety-related issues were reported.

Ocular adverse events (AEs) occurred in 26 (84%) subjects, all of which were mild in nature. All ocular AEs were resolved during the study period, except 1 AE of foreign body sensation, which was classified as unknown.

The most common treatment-related ocular AE was ocular hyperemia, which occurred in 21 hydralazine hydrochloride-treated eyes (7 [64%] subjects in the AMD group and 14 [70%] subjects in the normal/healthy group) but just 1 vehicle-treated eye. All instances of ocular hyperemia were resolved, with an average time to resolution of 1.85 days (range 1 to 4 days) for all subjects.

The incidence of ocular hyperemia found in eyes treated with the hydralazine hydrochloride formulation is consistent the known pharmacological effects of its active ingredient, an approved direct-acting antihypertensive drug with well-established peripheral vasodilatory effects.

The hydralazine hydrochloride ophthalmic solution was found to be slightly less comfortable than the vehicle immediately upon drop instillation in both subject groups, but no appreciable differences in comfort scores found by 30 minutes post drop instillation.

Choroidal blood flow, velocity and volume were assessed following the first dosing of test material on each day. On day 1, choroidal blood flow measurements were made at 30, 60, 120 and 240 minutes post-administration, on days 2 and 3, the measurements were made at the first two time-points only. Measurements were made using a Laser Doppler Flowmetry device, which is a state-of-the-art, non-invasive and quantitative approach for visualizing and measuring subfoveal choroidal blood flow.

The overall results indicate that the hydralazine hydrochloride ophthalmic formulation had pharmacological activity following topical ocular dosing:

There was a trend of increased mean choroidal blood volume and velocity values in hydralazine hydrochloride-treated eyes, which peaked approximately 2 hours after topical ocular dosing on day 1 and returned to baseline values approximately 4 hours after dosing (i.e., 2 hours later). In the AMD group, increases in blood volume were also found in hydralazine hydrochloride-treated eyes as early at 30 minutes post dosing on day 1.

For choroidal blood flow, there was a trend towards improved mean scores in hydralazine hydrochloride-treated eyes in AMD subjects. By contrast, in normal/healthy subjects both mean values and associated standard deviations (SDs) remained low at all time points on day 1.

Odds ratio analyses of the choroidal blood flow outcomes between the AMD and Normal groups for day 1 were evaluated. Tests for group differences were based on Fisher's exact test calculated using the FREQ procedure of SAS version 9.2 (SAS, 2009). For choroidal blood volume, odds ratios varied from 0.22 ($p=0.337$) at the 60 minute time point to 6.67 ($p=0.106$) at the 120 minute time point suggesting the possibility of higher hydralazine hydrochloride response in AMD patients at the 120 minute time point.

The results of this study demonstrate that a hydralazine hydrochloride ophthalmic solution is safe and generally well tolerated, with a low incidence of treatment-emergent AEs that were generally mild in severity and relatively evenly distributed among the 2 subject populations. There were no SAEs, no deaths, and no other clinically significant safety findings during the course of the study. Ocular hyperemia was the most commonly reported treatment-related ocular AE, reported by most subjects in this study. However, the incidence of ocular hyperemia is consistent with the peripheral vasodilatory effects of hydralazine hydrochloride and was not unexpected. Analysis of the choroidal blood data suggest that hydralazine hydrochloride may reach the back of the eye at the macular area to improve choroidal blood circulation following topical ocular instillation. Since impaired blood flow may be a contributing factor in the progression of dry AMD, these results suggest that hydralazine hydrochloride may be a useful therapeutic agent for the treatment of dry AMD.

Example 4

Hydralazine Formulation Single Dose Toxicity

Single dose ocular irritation studies with hydralazine ophthalmic formulations have shown a minimal to mild tendency for the formulation to produce ocular irritation according to the Draize procedure using the rabbit model.

Several studies were completed using various doses of hydralazine (0.0%, 0.5%, 1.0%, and 2.0% [w/w]) to assess the potential of hydralazine as an ocular irritant. The hydralazine formulations were prepared essentially as described in Example 1. Young adult female New Zealand white rabbits were grouped into a control and three treatment groups (n=3 for each group). A 0.1 mL dose (control or 0.5%, 1.0%, or 2.0% hydralazine formulation) was instilled in the right eye of each rabbit with the left eye serving as a control. The rabbit was used as a test model in these studies due to its demonstrated ability to respond to ocular irritants in a manner that is valuable in prediction of a similar human response. The rabbit model is known to be somewhat more sensitive to some irritants than the human (Milllichamp 1999a, Millichamp 1999b). A buffered pH of 4.2 and preservative agents known to cause transient ocular irritation were employed to ensure stability and dose integrity.

Overall, all formulations tested showed minimal ocular irritation in primary eye irritation studies using the rabbit model. The formulation tested with 2.0% hydralazine demonstrated slightly greater irritation than formulations containing 0.0%, 0.5%, or 1.0% hydralazine hydrochloride; each concentration showed a maximum mean total Draize score of 2.0 and was classified as minimally irritating.

Example 5

Hydralazine Formulation Repeated Dose Toxicity

Hydralazine hydrochloride ophthalmic solutions were prepared essentially as described in Example 1 at concentrations of 0.0% (vehicle), 0.5% hydralazine hydrochloride, 1.0% hydralazine hydrochloride, and 2.0% hydralazine hydrochloride. The formulation, vehicle or control was administered daily for 28 days to the designated eye of forty Dutch Belted rabbits (5 males and 5 females per group) as shown in Table 2.

TABLE 2

Summary of Repeated Dose Toxicity Studies in Animals

| | | Dose | |
| --- | --- | --- | --- |
| Group | Treatment | Left Eye | Right Eye |
| 1 | Vehicle (0.0% hydralazine hydrochloride) | 40 µL/vehicle | 40 µL/saline |
| 2 | 0.5% hydralazine hydrochloride | 40 µL/0.5% | 40 µL/vehicle |
| 3 | 1.0% hydralazine hydrochloride | 40 µL/1.0% | 40 µL/vehicle |
| 4 | 2.0% hydralazine hydrochloride | 40 µL/2.0% | 40 µL/vehicle |

Group 1 received vehicle in the left eye and saline in the right eye, while Groups 2-4 received hydralazine hydrochloride (either a low [0.5% hydralazine, w/w, 0.2 mg/kg/dose], mid [1.0% hydralazine w/w, 0.4 mg/kg/dose], or high [2.0% hydralazine, w/w, 0.8 mg/kg/dose] dose) in the left eye and vehicle in the right eye.

After 28 days of topical ocular treatment, application of the vehicle or hydralazine hydrochloride did not result in the development of significant doserelated toxicologic changes, including assessments of routine ocular evaluations, tonometry, body weight, organ weight, clinical chemistry, ocular pathology, inflammation, degeneration, or histologic evidence of toxicity in the eyes of Dutch Belted Rabbits.

The highest dose concentration administered in this study was the maximum concentration possible that could be prepared using the ophthalmic preparation vehicle while maintaining good solubility of the hydralazine active pharmaceutical ingredient. The maximum dose volume that was administered was the maximum volume that can be applied to the eye in the rabbit animal model. This resulted in a maximum daily dose of 0.8 mg/kg/dose being administered using a total dose volume of 40 µL per dose.

Food consumption was similar among all groups and there were no statistically significant differences in body weight between groups. No treatment-related findings were noted on routine physical and clinical examinations. There were no unscheduled deaths.

There were no statistically significant differences, in either male or female rabbits, between Group 1 and Groups 2-4 in macroscopic ocular examination findings, for the measurements conducted on Day 28.

Light reflexes were examined pre dose and on Day 29. All pupillary responses at all time periods were normal for all treatment groups.

A modified Hackett and McDonald microscopic ocular grading system (Hackett 1996) was applied to ocular findings following the use of a slit-lamp biomicroscope, which included insertion of a blue filter to assess for fluorescein dye retention. For any evaluated microscopic ocular examination parameter, there were no statistically significant differences, in either male or female rabbits, between Group 1 and Groups 2-4 during the pre dose or Day 29 study measurement periods.

Mean tonometry (Tono-pen; Reichert Ophthalmic Instruments, Depew, N.Y.) readings of IOP in control and test rabbits pre-dose and on Day 29 were between 15-25 mmHg, which is within the normal physiologic range. Prior to termination (Day 29), 1 parameter showed a statistically significant difference: When compared with Group 1 means, the left eye mean IOP for Group 4 females was increased, though the mean value (22 mmHg) was within the normal physiologic range; furthermore, the left eye mean IOP was not different from the placebo-treated right eye mean IOP in Group 4 females.

No statistically significant differences for hematologic indices occurred between groups during any period of the study other than a low log transformed absolute eosinophil count in female rabbits in Groups 2 and 4 in the Day 29 samples.

No statistically significant differences for serum chemistry indices occurred between groups during any period of the study with the exception of low cholesterol values in females in Groups 2 and 4 in the Day 29 samples.

There were no statistically significant differences, in mean organ weights and relative organ weights, for both male and female rabbits, between Group 1 and Groups 2-4. There were no significant gross pathologic changes observed during necropsy that could be considered to be dose-related.

Forty (40) sets of hematoxylin and eosin stained slides consisting of temporal, central (including optic nerve), and nasal sagittal sections of each eye, lacrimal glands, and ocular adnexa underwent histopathologic examination by a board-certified veterinary ophthalmologist. In all groups, findings consisted of conjunctival lymphoid follicles, focal or diffuse loss of corneal epithelium, and/or retinal folds. These findings occurred in nearly equal frequency between the right and left eyes and among Groups 1 through 4 and are associated with processing artifacts and considered incidental findings. Daily application of up to 2.0% hydralazine hydrochloride or vehicle did not result in the development of ocular pathology, inflammation, degeneration, or histologic evidence of toxicity in the eyes of Dutch Belted Rabbits after 28 days of topical ocular treatment.

Based on the results obtained from these ocular dosing studies performed with the proposed formulation, it would appear that formulated doses of hydralazine hydrochloride of up to 2.0% w/w should be reasonably well tolerated and safe for use in the human eye.

Example 6

Effect of Hydralazine Formulation on Choroidal Blood Flow

A 1.0% hydralazine ophthalmic solution was prepared essentially as described in Example 1.

Twelve female New Zealand white rabbits, weighing 2.5-3.0 kg, were anesthetized with 35 mg/kg ketamine and 5 mg/kg xylazine intramuscularly. Half of the initial dose was given hourly to maintain anesthesia.

An ocular hypertensive model was created by raising the intraocular pressure of the left eye to 40 mmHg by anterior chamber puncture to establish the ocular hypertensive model The left ventricle was cannulated through the right carotid artery for the injection of microspheres (IMT-Stason Laboratories, Irvine Calif.). The femoral artery was cannulated for blood sampling.

50 μL of a saline solution (n=5), as a control, or the 1.0% hydralazine ophthalmic solution (n=7) was instilled topically in the left eye. Choroidal blood flow was measured with colored microspheres at 0, 30, 60, and 120 minutes thereafter. At each time point, 0.2 mL of different colored microspheres was injected into the left ventricle as a reference, and blood samples were taken from the femoral artery for exactly one minute following injection of the microspheres. The blood sample was collected in a heparinized tube, and the volume was recorded.

The rabbits were euthanized with an injection of 100 mg/kg pentobarbital sodium after the last blood sampling. The left eyes were enucleated and choroids excised. The tissue samples were weighed, digested, and the microspheres in the tissue were counted with a hemocytometer. The blood flow of each tissue at a certain time point was calculated using the following equation:

$$Qm = (Cm \times Qr)/Cr$$

where Qm is the blood flow of a tissue in terms of μL/min/mg, Cm is the microsphere count per mg of tissue, Qr is the flow rate of the blood sample in terms of μL/min, and Cr is the total microsphere count in the referenced blood sample.

The 1.0% concentration of hydralazine eyedrops was found to significantly enhance choroidal blood flow in rabbits 30 and 60 min after drug instillation as compared with the control (P<0.05), with the results shown in FIG. 1.

Example 7

In Vivo Effect of Hydralazine Formulation on Laser-Induced Choroidal Neovascularization 0.5%, 1.0%, and 2.0% hydralazine ophthalmic solutions was prepared essentially as described in Example 1.

Twenty-five Brown-Norway rats, weighing 150-180 g, were anesthetized with 35 mg/kg ketamine and 5 mg/kg xylazine intramuscularly. Pupils were dilated with a topical application of 1% tropicamide (Bausch & Lomb; Tampa, Fla.) and 2.5% phenylephrine. The ocular fundus was visualized with a VOLK super pupil XL biomicroscopy lens (Keeler Instrument, Inc., Broomall, Pa.) A double frequency Nd:YAG laser (Laserex LP3532; Lumenis Inc., Salt Lake City Utah) was used at a 532 nm wavelength to penetrate Bruch's membrane. The spot size was 100 μm. Power delivered was 200 mW, applied for 0.15 second exposure. Six lesions were made to the ocular fundus at approximately equal distances from the optic nerve. Only laser spots with bubble formation were included. Lesions with substantial retinal hemorrhage were excluded.

Hydralazine eyedrops comprising 0.5% (n=5), 1.0% (n=10), or 2.0% (n=5) hydralazine hydrochloride or saline eyedrops (n=5) were instilled bilaterally 3 times per day for 4 weeks immediately after laser treatment. Administration of drug immediately following laser treatment is a considered to be a better model for dry AMD and differs from the normal laser-induced CNV (wet AMD) model in which drug is administered after around 2 weeks following laser insult at the point that bleeding occurs.

Fluorescein angiography was performed after four weeks of treatment in anesthetized animals with dilated pupils using a Digital Fundus Camera (TRC-50 EX: Topcon, Japan) and standard fluorescein filter. 0.3 ml of 10% fluorescein isothiocyanate-dextran (Sigma-Aldrich Inc., St. Louis, Mo.) was injected intravenously via the hypoglossal vein at 0.14 mL/100 g of body weight. Fluorescein pictures were captured within 20 minutes, and pictures with the clearest quality were chosen for measuring the areas of CNV formation using Imagenet 2000 digital imaging systems (Topcon Medical Systems, Inc., Paramus N.J.) with the results shown in FIG. 2.

After fluorescein angiography pictures were captured, rats were sacrificed and the eyes were enucleated and fixed in 10% phosphate-buffered formalin. The cornea and lens were excised and the entire retina was carefully dissected. Radial cuts (usually 4-6) of the choroid were made from the edge of the choroid to the equator, and the eyecup was flat mounted with the choroid facing up. Flat mounts were imaged by fluorescence microscopy on an Axioskop microscope (Zeiss, Thornwood, N.Y.), and Image-Pro Plus software (Media Cybernetics, Silver Spring, Md.) was used to measure the area of CNV with the results shown in FIG. 3.

After 4 weeks of treatment, all of the treatment groups demonstrated significantly reduced CNV area (P<0.05 for 2.0%; P<0.01 for 0.5% and 1.0%) on fluorescein staining. The same results were demonstrated on the choroidal flat mount (P<0.01 for all groups).

In both of these analyses, significant reduction was seen at least with the 1.0% hydralazine hydrochloride ophthalmic solution, which also had shown significant reduction in choroidal blood flow.

Example 8

In Vitro Effect of Hydralazine Formulation on Tube Formation

Endothelial cells will form tube-like structures in vitro when grown on a matrix gel surface under the proper growth conditions. This study measured the ability of hydralazine formulations to inhibit tube formation in vitro and represents an in vitro anti-angiogenesis assay.

Human Umbilical Vein Endothelial Cells (HUVEC) were purchased from ScienceCell (San Diego, Calif.). The medium was prepared with endothelial basal medium (EBM-2; Lonza Walkersville Inc., Walkersville, Md.), 10% fetal cattle serum, and endothelium growth medium (EGM-2 SingleQuots; Lonza Walkersville Inc.), which contains 2 mM glutamine, 100 units/mL penicillin and 100 μg/mL streptomycin. Hydralazine at concentrations of 0 (control), 1, 3, 10, 30, and 100 μg/mL was added to the medium at time 0. Cells were cultured at 37° C. on a 2.5% matrix gel in an atmosphere of 5% $CO_2$ and 95% air, and HUVEC were incubated for 48 hours. Images of the cell morphology were obtained using conventional photomicroscopy (Zeiss). The in vitro experiment studying tube formation by HUVEC was repeated 3 times.

Treatment with 1 mg/mL of hydralazine was found not to be different from the control. With 3 μg/mL of hydralazine some HUVEC failed to grow into tubes, and this effect became most apparent at 30 μg/mL of hydralazine. Hydralazine at 100 μg/ml caused apoptosis.

Example 9

In Vitro Effects on Sodium Iodate-Induced Rat Model of Nonexudative Age-Related Macular Degeneration Intravenous injection of sodium iodate ($NaIO_3$) results in selective toxicity to cells in the retinal pigment epithelium (RPE) (Noell 1953). The effects on the RPE are dependent on the dose of $NaIO_3$. This approach was used to create a rat model of nonexudative AMD in which the potential protective effects of hydralazine formulations could be evaluated.

A human retinal pigment epithelial cell line (ARPE-19; American Type Culture Collection, Manassas, Va.) was used to evaluate the toxicity of $NaIO_3$ in vitro. Cells were incubated at 37° C. in a humidified atmosphere of 5% $CO_2$ and 95% air. Growth medium was composed of 1:1 mixture of Dulbecco's Modified Eagle's Medium (DMEM) and Ham's F12 medium containing 1.2 g/L sodium bicarbonate, 2.5 mM L-glutamine, 15 mM HEPES, 0.5 mM sodium pyruvate, and 10% fetal bovine serum (all from Invitrogen). Confluent cultures were harvested by digestion with 0.25% trypsin-0.2 g/L ethylene diamine tetra acetic acid (EDTA) (Sigma-Aldrich). For the cell proliferation assay, ARPE-19 cells were grown in 96-well tissue culture plates overnight. Medium was then replaced by fresh medium containing various concentrations of $NaIO_3$ (0, 0.01, 0.03, 0.1, 0.3, 1, 3, 10, 30, 100 μg/mL). After incubation for 48 hours, cells were washed with Dulbecco's phosphate-buffered saline 1 time and further incubated with 100 μL of 10% 3-(4,5-dimethylthiazol-2-yl)-2,5diphenyl tetrazolium bromide (MTT) for exactly 4 hours. Media was then removed by aspiration, 100 μL of DMSO was added into each well, and dishes were shaken for 2 minutes to dissolve the cells and colored formazan product. Light absorbency in each well was read at 570 nm (OD570) using a SpectraCount plate reader (Packard BioScience, Meridan, Conn.). The effect of the added $NaIO_3$ on cell viability was calculated as the ratio of the OD570 of the $NaIO_3$-exposed cells to the OD570 of the control cells, expressed as a percentage of the control. The experiment was repeated 6 times using 6 wells for each group during each experiment.

The MTT colorimetric assay was used to quantify the toxic effects of $NaIO_3$ on RPE cells in vitro. At $NaIO_3$ concentrations of 10 μg/mL or lower, there was no significant reduction in the growth of the cells. $NaIO_3$ concentrations of 30 μg/mL and 100 μg/mL reduced the number of viable ARPE-19 cells to approximately 65% and 40%, respectively, of the level observed in the control.

Example 10

In Vivo Rat Model of Sodium Iodate-Induced Nonexudative Age-Related Macular Degeneration For establishment of the $NaIO_3$ model, 28 eight-week-old male Brown Norway rats (Texas A&M University, Texas) were housed in a standard animal room with a 12:12 hour cyclic lighting schedule. Animals were fed with normal food and water. All procedures conformed to the ARVO Resolution on the Use of Animals in Ophthalmic and Vision Research.

$NaIO_3$ (Sigma-Aldrich) was dissolved in saline at a concentration of 3.0%. Rats received a single injection of $NaIO_3$ through the sublingual vein at doses of 0, 7.5, 15, 20, 30, 40, and 60 mg $NaIO_3$/kg of body weight (4 rats each per concentration group).

Functional (ERG, fundus pictures, and fluorescein angiography) and histological changes were examined selectively at time points between 3 and 56 days post injection.

For the experiments with hydralazine 1.0% ophthalmic solution (Pam Lewis Associates, San Antonio, Tex.), the normal group was instilled bilaterally with saline alone without $NaIO_3$ injection. The $NaIO_3$ group was instilled with saline alone after a single injection of 35 mg/kg $NaIO_3$, and the hydralazine 1.0%+$NaIO_3$ group was instilled with hydralazine 1.0% eyedrops after an injection of 35 mg/kg $NaIO_3$. All eyedrops were instilled 3 times per day for 4 weeks, beginning immediately post injection.

Functional testing of the retina was performed using an EPIC-2000 Visual Electrodiagnostic Testing System (LKC Technologies, Inc., Gaithersburg, Md.). The flash stimulation was supplied by a Grass Instruments PS22 photic stimulator (Grass Instruments Co., Waltham, Mass.). The photostimulator was positioned 5 inches from the eye. At each endpoint (2 and 4 weeks), the electroretinogram (ERG) c-wave was measured in all rats as follows. Rats were dark adapted overnight, then anesthetized with 35 mg/kg ketamine plus 5 mg/kg xylazine given intramuscularly. Half of the initial dose was given each hour thereafter to maintain anesthesia. The pupils of all rats were dilated with 1 drop each of atropine 1%, tropicamide 1%, and phenylephrine 2.5%. Before recording, 1 drop of opticaine was used for surface anesthetization. All animals were kept warm during ERG measurement.

The rat retina was irreversibly damaged by high doses of $NaIO_3$, from neural retina layers to photoreceptor and RPE cell layers. High doses of $NaIO_3$ induced severe retina toxicity; with lower doses, not as many or as severe changes were found. These results indicate that a moderate dose of $NaIO_3$ would be suitable for the animal model for treatment of dry-AMD; 30 mg/kg to 40 mg/kg $NaIO_3$ would be optimal for use in this animal model.

Each rat was measured by DC-ERG recording first, then by ACERG recording. For AC-ERG recording, an Ag/AgCl electrode was placed gently in contact with the cornea as a reference electrode. A drop of NaCl 0.9% was used between the cornea and the electrode to establish stable signal conductance. A stainless steel long electrode was inserted beneath the forehead skin between the 2 eyes, and another stainless steel short electrode was inserted subcutaneously in the leg as a ground electrode. A single scotopic white flash (20 ms duration) was used to elicit ERG and b-waves. The intensity of the stimulus was 628 cds/m2 and bandpass filtered from 0.3 to 500 Hz. For DC-ERG, per previously described methods (Peachey et al., 2002, Vis Neurosci, 19(6):693-701), a 1-mm diameter glass capillary tube with filament (Sutter Instruments, Novato, Calif.) that was filled with Hank's balanced salt solution (Invitrogen, Carlsbad, Calif.) was used to make contact with an Ag/AgCl wire electrode with an attached connector. The capillary tube was in contact with the rat's corneal surface. Another similar electrode placed on the surface of the contralateral eye served as a reference lead. Responses were amplified (DC-100 Hz, gain=1000×) (DP-301; Warner Instruments, Hamden, Conn.) and digitized at 10 Hz or 1000 Hz. Data were analyzed by iWORX LabScribe Data Recording Software (iWorxOCB Sciences, Dover, N.H.). Light stimuli were derived from an optical channel using a fiber-lite high intensity illuminator (Dolan-Jenner Industries, Boxborough, Mass.), with neutral density filters (Oriel, Stratford, Conn.) placed in the light path to adjust stimulus luminance. The stimulus luminance used in this experiment was 3.22 log cd/m2 and 4 minutes in duration. Luminance calibration was performed with a Minolta (Ramsey, N.J.) LS-110 photometer focused on the output side of the fiber optic bundle where the rat eye was located.

During AC-ERG recording, the a-wave was measured from baseline to the first negative trough; maximum b-wave amplitude (Vbmax) was measured from the first negative trough (a-wave) to the first positive peak of the b-wave. For the DC-ERG recording, the second positive peak that followed the b-wave was the c-wave, the amplitude of which was measured from the trough after the bwave (which was the after potential; AP) to the peak of the c-wave. The amplitude of fast oscillation (FO) was measured from the c-wave peak to the FO trough. The light peak (LP) was measured from the FO trough to the LP maximum (Peachey 2002).

A digital fundus camera (TRC-50EX; TOPCON) and Imagenet 2000 digital imaging system (Topcon Medical Systems) were used to capture retinal colored pictures and fluorescein angiograms. When using fluorescein angiography, 10 mg of fluorescein sodium was injected through the hypoglossal vein of the rats. Anesthesia and pupil dilation were performed as described above.

After functional examination, all rats were sacrificed. In approximately 16 rats (from different hydralazine treatment groups), the eyes were removed and fixed in 2.5% glutaraldehyde for 2 hours and then in 5% formalin overnight; 1 eye from each animal was used for histology and immunohistology studies, and the other eye was prepared for autofluorescence measurement on flat mounts. For histologic assessments, paraffin-embedded tissues were sectioned at 3 μm thickness. Eyes were incised from the cornea to the optic nerve head along the vertical meridian, then stained with hematoxylin and eosin. An Axioskop microscope (Zeiss) was used to capture the images. For preparation of flat mounts, 1 eye from each animal was enucleated. After fixation, the anterior part of the eye, as well as the cornea, lens, and sensory retina, were gently removed and the remaining eyecup was washed in PBS. Four cuts were made from edge to center to assist in flattening the eyecup onto a glass slide. The autofluorescence of the RPE in flat mount was studied and captured on a confocal microscope (Zeiss LSM510; Zeiss) using an Argon laser (wavelength 488 nm).

A Student t test was used for statistical analysis. A 1-tailed t test was used for the in vivo experiment, and a 2-tailed t test was used for the in vitro assay.

Fluorescein Angiography and Fundus Photography

Hyperfluorescence in the whole retina was observed as early as 3 days after injection in the 60 mg/kg $NaIO_3$ dose group; however, there were no obvious changes seen in fundus pictures at this early time point. Partial retinal hyperfluorescence could be seen at 3 days after injection in both the 40 mg/kg and 30 mg/kg $NaIO_3$ dose groups, but the effect was not as pronounced as that observed in the 60 mg/kg group. Hypofluorescence was evident in the peripheral retina at longer times post injection (defined as between 28 and 56 days). Yellow dots or scars, which were related to the dose of $NaIO_3$ and were indicative of necrosis, could be seen as early as 7 days in all 3 groups from the peripheral to the central retina. In the 20 mg/kg $NaIO_3$ group, changes were not obvious until 28 days in both the fundus pictures and fluorescein angiography.

Effects of $NaIO_3$ on ERG

Single injections of $NaIO_3$ at doses of 40 or 60 mg/kg had dramatic effects on the on the maximum b-wave amplitude (Vbmax) that were apparent by 3 and 7 days after injection. The ERG b-wave disappeared completely in the 60 mg/kg group by 28 days after treatment. In the 40 mg/kg group, the b-wave magnitude decreased significantly by 3 days post injection and continued to decrease at all subsequent time points; at 56 days, there was no measurable b-wave. Twenty (20) mg/kg $NaIO_3$ decreased the bwave magnitude at 7 days, but it recovered to the level seen in the control group at 14 days and thereafter.

$NaIO_3$ doses of 15 or 7.5 mg/kg did not suppress any of the ERG waves at any time point. A single injection of 30 mg/kg $NaIO_3$ caused a decrease in all of the ERG waves at 7 days post injection. The a-wave and b-wave signals in the 30 mg/kg dose group appeared to recover at the later time points (14 days and 28 days). In contrast, the c-wave signal was suppressed at all time points after the 30 mg/kg $NaIO_3$ injection. The FO and LP indices were measured relative to the c-wave and reflect the $NaIO_3$ dose response seen in the c-wave data.

The ERG c-wave originates in the RPE. The suppressive effect of $NaIO_3$ on the ERG c-wave signal is consistent with the known toxic effects of this compound. The long-term suppression of the ERG c-wave signal supports the use of this rat model for the study of nonexudative AMD.

Effects on Retinal Histopathology

Some retinal necrosis appeared at 3 days post injection in the 30 mg/kg $NaIO_3$ group, which became more serious in the higher dose groups (i.e., 40 or 60 mg/kg $NaIO_3$) or at longer times after injection. There were no histological changes evident in retinas from rats in the lower dose groups (<30 mg/kg). Similarly, on the retina flat mount, examination of the RPE monolayer showed evidence of necrosis at 3 days after injection in the higher dose groups; no significant changes were seen in the 30 mg/kg $NaIO_3$ and lower dose groups. A decrease in the density of both RPE cells and photoreceptor cells was evident in retinas from rats in the 60 mg/kg group at 3 days or longer post injection. In the 40 mg/kg dose group, similar changes were observed beginning at 7 days after injection. A decrease in the number of melanin granules in the RPE cells was noted in the 30 mg/kg $NaIO_3$ dose group beginning at 7 days post injection. No obvious changes were seen in the 20 mg/kg $NaIO_3$ dose group.

In flat mount preparations, laser-induced autofluorescence of the RPE cells was measured by confocal microscopy. After doses of 30 mg/kg $NaIO_3$ or higher, small holes were observed in the RPE at 3 days, which increased in number at longer times post injection. These defects in the RPE autofluorescence signal indicate regions of necrosis of RPE cells. In the 20 mg/kg $NaIO_3$ dose group, small holes in the RPE autofluorescence were observed beginning at 7 days, and were fewer in number than that observed in the higher dose groups.

Ability of Hydralazine Formulations to Block $NaIO_3$-Induced Damage

Based on the results of the time- and dose-dependence experiments described above, a concentration of 35 mg/kg $NaIO_3$ and a time point of 28 days were as chosen for the experiment to test the ability of hydralazine to block the effects of $NaIO_3$ on rat ERG patterns. The normal group did not receive any $NaIO_3$ and received saline-only eyedrops. At 4 weeks after injection of $NaIO_3$ at a dose of 35 mg/kg, the ERG c-wave amplitude fell markedly to 31% of that in the control group (P<0.01). The ERG c-wave amplitude of the hydralazine 1.0%+$NaIO_3$ group fell to 50% of that of the control group (P<0.05). The magnitude of the c-wave signal observed in the 1.0% hydralazine+$NaIO_3$ group was significantly greater than the signal in the $NaIO_3$-only group (P<0.01) (FIG. 4). This demonstrates a protective effect of the hydralazine 1.0% eyedrops in this model; the hydralazine blocked (or restored) 61% of the damage to the RPE cells caused by the $NaIO_3$ injection.

Example 11

Antioxidant Effect of Hydralazine on Retinal Pigment Epithelial Cells Quantitative Determination of Cell Damage Induced Oxidative Stress The human RPE cell line ARPE-19 (ATCC; Manassas, Va.) was cultured in Dulbecco's Modified Essential Medium (DMEM) supplemented with 10% fetal bovine serum, 50 units/mL penicillin-streptomycin and 2.5 mM glutamine at 37° incubation with 5% $CO_2$. The cell line was not transformed and had structure and function properties characteristic of RPE in vivo. The cells were seeded into 96-well plates, and subconfluent cell monolayers were studied within 3 to 10 passages. Before starting the experimental procedures, the medium was removed and replaced with phenol red-free low-glucose DMEM supplemented with 1% calf serum, 0.06% glutamine, and 1% penicillin-streptomycin.

Cultured ARPE-19 cells, at a concentration of 1×105 cells/mL, were seeded into 96-well plates. The cells were used for experiments when they reached 80% confluence to prevent contact inhibition. The ARPE-19 cells were exposed to chemical agents designed to simulate oxidative stress ($H_2O_2$, t-BHP) or hypoxia ($NaIO_3$), and the ability of various concentrations of hydralazine (1, 3, 10, 30, or 100 µg/mL) to block the damage was measured.

For the oxidative stress and hypoxia experiments, the particular chemical agent and the hydralazine formulation were both added to the wells (or just the chemical agent for the controls), and the plates were incubated at 37° C. for 24 hours. Cell viability was assessed using a 3-(4,5-dimethylthiazol-2-yl)-2,5-diphenyl tetrazolium bromide (MTT) assay to determine the relative number of living cells in each culture (only live cells have the mitochondrial enzyme activity needed to convert the MTT molecule into the dark purple substance formazan) (Swanson, 1992, Neurosci Lett, 147(2):143-146)). After the 24-hour exposure, the MTT reagent solution (5 mg/mL) was added to each well in a ratio of 1:10 MTT reagent:culture medium volume. The cultures were incubated with the MTT reagent for 3 hours at 37° C. At the end of incubation, the MTT solution was removed, and 0.1 mL of dimethyl sulfoxide (DMSO) was added to each well to solubilize the purple formazan product. The proportion of viable cells was determined by measuring the optical density (OD) of each sample at 570 nm (A570) using a SpectraCount plate reader (Packard BioScience, Meridan, Conn.). The relationship between the OD readings in the MTT colorimetric assay and the exact cell number was determined by seeding cells at identical densities and then performing the MTT assay and manual hemocytometer cell counts on parallel replicate cultures. Trypan blue was added to the hemocytometer cultures so that only viable, dye-excluding cells were counted. This approach enabled the establishment of a standard curve for A570 versus cell number.

Chemical hypoxia was induced by using a modified method described by Swanson et al. (Swanson 1992; Varming 1996). RPE cells were washed and replaced with fresh DMEM-F12 medium containing various concentrations of NaN3 (0.1 mM-100 mM). The hydralazine formulation was then added and the cultures and test agent were incubated for 24 hours at 37° C. Reactions were stopped by washing out the medium. MTT reagent solution (5 mg/mL) was added in a ratio of 1:10 MTT reagent:culture medium volume and then incubated for 3 hours at 37° C. At the end of incubation, the MTT solution was removed, and 0.1 mL of DMSO was added to each well to solubilize the purple formazan product. The proportion of viable cells was determined by measuring the OD of each sample at 570 nm using a SpectraCount plate reader (Packard BioScience, Meridan, Conn.).

All data were presented as mean±standard error. A non-paired Student t test was performed to analyze the significance between 2 means at a certain time point. The differences were considered significant at P<0.05. Results for nitric oxide measurements were expressed in µM nitrite and nitrate per $1×10^6$ cells.

Effect of Hydralazine on tBHP-Induced Toxicity

Cell viability of the controls (cells treated with tBHP alone) was reduced to 89.90%±2.80% after insult with 0.01 mM tBHP and to 55.80%±4.08% after insult with 0.03 mM tBHP. Hydralazine formulations inhibited tBHP-induced cell damage in an apparent concentration dependent manner after insult with 0.01 mM and 0.03 mM of tBHP. The maximum viability protection effect after insult with both 0.01 and 0.03 mM tBHP was observed with 100 µg/mL of hydralazine (109.99%±2.41% for 0.01 mM tBHP; 100.84%±13.00% for 0.03 mM tBHP); as compared with the controls, these differences were statistically significant (P<0.001). A statistically significant protection effect (P<0.01) was also observed with 30 µg/mL of hydralazine after insult with 0.01 mM tBHP and with all concentrations of hydralazine (P<0.001) after insult with 0.03 mM tBHP.

Effect of Hydralazine on $H_2O_2$-Induced Toxicity in ARPE-19 Cells

Cell viability of the controls (cells treated with $H_2O_2$ alone) was reduced to 48.74%±2.40% after insult with 0.3 mM $H_2O_2$ and to 41.28%±0.80% after insult with 1.0 mM $H_2O_2$. The hydralazine formulations inhibited $H_2O_2$-induced cell damage in an apparent concentration dependent manner after insult with 0.3 mM and 1.0 mM of $H_2O_2$. The maximum viability protection effect after insult with 0.3 mM $H_2O_2$ was observed with 30 µg/mL of hydralazine (74.30%±0.80%); as compared with the control, this difference was statistically significant (P<0.001). The maximum viability protection effect after insult with 0.3 mM $H_2O_2$ was observed with 30 µg/mL of hydralazine (68.04%±0.67%); as compared with the control, this difference was statistically significant (P<0.001). A statistically significant protection effect was also observed with 100 µg/mL (P<0.001) and 10 µg/mL (P<0.001) of hydralazine after insult with 0.3 mM $H_2O_2$ and with 100 µg/mL (P<0.001) of hydralazine after insult with 1.0 mM $H_2O_2$.

Effect of Hydralazine on Hypoxia-Induced Cell Damage in ARPE-19 Cells

In vitro hypoxia treatment was carried out using a ProOx hypoxia system. ARPE-19 cells were allowed to attach overnight and were then exposed to hydralazine (0.1-100 µg/mL) under normoxic or hypoxic condition for 24, 48, and 72 hours. In hypoxia, oxygen concentrations of 1% $O_2$ and 5% $CO_2$ were maintained using a temperature- and humidity-controlled environmental C-chamber by $O_2$ and $CO_2$ controllers (ProOx Model 110 and ProCO2 Model 120; BioSpherix Ltd., Redfield, N.Y.) with $N_2$ and $CO_2$ gas sources. Reactions were stopped by washing out the medium, and 5 mg/mL MTT at a dilution of 1:10 based on the volume of culture medium was added for 3 hours at 37° C. At the end of incubation, the MTT solution was removed, and the cells were dissolved in 0.1 mL/well DMSO. The proportion viable cells were determined by measuring the OD of each sample at 570 nm using a SpectraCount plate reader (Packard BioScience, Meridan, Conn.).

Cell viability of the controls (cells exposed to 1% $O_2$ and 5% $CO_2$ without hydralazine treatment) was 98.91%±0.56% and 97.45%±0.52% at 48 and 72 hours, respectively. Hydralazine formulations significantly reversed hypoxia-induced cell damage as compared with controls. The maximum reversion effects were seen with 1 µg/mL of hydralazine at 48 hours (101.21%±0.54%; P<0.001) and 72 hours (103.55%±1.75%; P<0.001).

Example 12

Effect of Hydralazine on Nitric Oxide (NO) Production in ARPE-19 Cells

Following exposure to a hydralazine formulation and incubation with chemicals as described in the previous section, samples of phenol red and dexamethasone-free culture media were extracted and levels of nitrite and nitrate, the relatively stable end products of nitric oxide (NO), were determined using the nitrite/nitrate Greiss reagent system. Fifty (50) µL aliquots of phenol red-free culture medium in 60 µL assay buffer were incubated with 10 µL each of nitrate reductase preparation and nitrate reductase cofactor preparation (proprietary concentrations), which converts nitrate to nitrite, for 60 minutes at room temperature in 96-well microassay plates. After the required incubation time, 10 µL of DAN reagent was added to each well, incubated for 10 minutes and then the reaction was stopped with 20 µL of NaOH added to each well. The total nitrite/nitrate was determined by measuring the OD of each sample at 540 nm using a SpectraCount plate reader (Packard BioScience, Meriden, Conn.). Data were calculated with nitrate standard curve.

No significant effect of NO production was detected after treatment with the hydralazine formulation.

Example 13

Treatment of Non-Exudative Age-Related Macular Degeneration (Dry AMD) with Hydralazine Hydrochloride Ophthalmic Formulation The study is a vehicle controlled, double masked, single center study in which a single eye of 60 human individuals with mild to moderate nonexudative AMD is randomly assigned to receive either topical hydralazine hydrochloride 1% or a vehicle control three times a day for 2 years. The analysis of the primary and secondary endpoints are conducted when all subjects have completed 12, 18 and 24 months.

A 1% hydralazine hydrochloride ophthalmic solution is supplied as a colorless isotonic solution containing 1% (10 mg/mL) hydralazine hydrochloride, which is filter sterilized. Inactive ingredients include: edetate disodium, sodium chloride, and propylene glycol in an acetate buffer solution (all United States Pharmacopeia [USP] grade) at a pH range of 3.8-4.4 and osmolality range of 300-340 mOsmol/kg in addition to benzalkonium chloride and methyl parabens as preservative.

The vehicle is manufactured in an identical manner to the hydralazine hydrochloride ophthalmic solution but without the active agent. Each bottle contains 7 mL and bottles have a dropper that measures 40 to 50 microliters per drop.

The formulation and vehicle control are self-administered by the patient three times a day: morning, afternoon, and evening. Each drop consists of a 40-50 µL drop of 1% hydralazine hydrochloride active ingredient in a sterile saline vehicle with preservatives. The drug or vehicle is self-administered by instillation of one drop into the study eye TID for 24 months.

Pre-treatment ocular examinations (treatment eye only) are performed and include: ETDRS visual acuity, refraction, intraocular pressure, pupil assessment, slit lamp examination (assess lids/lashes, conjunctiva/sclera, cornea, anterior chamber, iris, lens, anterior vitreous), and dilated fundoscopy (assess optic nerve, vitreous, vessels, macula, and periphery). Additional testing of the treatment eye includes: dark adaptation, flavoprotein fluorescence, lipofuscin fluorescence, color fundus photography, OCT, and choroidal flowmetry. At one month and three months after treatment, an ocular examination is performed in the study eye including: ETDRS visual acuity, refraction, intraocular pressure, pupil assessment, slit lamp examination (assess lids/lashes, conjunctiva/sclera, cornea, anterior chamber, iris, lens, anterior vitreous), and dilated fundoscopy (assess optic nerve, vitreous, vessels, macula, and periphery). At 6, 12, 18 and 24 months, an ocular examination of the treatment eye is performed as well as testing of the treatment eye.

The primary efficacy measure, dark adaptation (rod intercept) is analyzed by a comparison of the treatment groups on the change from baseline in rod intercept, by computing the slope (best linear fit) of the rod intercept data across visits to yield an annualized rate of change. Dark adaptation allows for quantification of outer retinal parameters such as rod function. It is measured with a computerized dark adaptometer (AdaptDx; Apeliotus Technologies, Atlanta, Ga., USA) using methods described by Jackson et al. (J Ocul Biol Dis Inform., 1:7-11, 2008). Dark adaptation functions are plotted using Igor Pro (Wavemetrics, Portland, Oreg., USA). The primary endpoint is the rod intercept, which is measured in minutes and presented on the instrument. Additional measures include the cone sensitivity plateau value, rod-cone break, and rod sensitivity recovery slope. The dark adaptation testing is performed at the baseline, and 6, 12, 18, and 24 months after treatment.

The primary efficacy analysis is conducted on the 12 month data. The study continues to be double masked through to month 24 with a further analysis for efficacy and safety at months 18 and 24.

If a subject contributes only one measure, a slope of zero is assigned. The difference between groups in mean slope is tested using an analysis of covariance model where treatment assignment is a fixed factor and the baseline rod intercept is a covariate. Sensitivity analyses is performed with different methods of imputation for missing slopes and those assigned a value of zero if there is differential missingness between groups.

A sample size of 30 in each group has 90% power to detect a ratio of the difference in means to the common standard deviation of at least 0.863 using a two group t-test with a 0.05 two-sided significance level.

Example: If the SD is 4 minutes and the difference between the groups is 3.45 minutes per year, then with 30/group there would be 90% power (3.45/4.00=0.863).

Secondary efficacy measures include: ETDRS visual acuity, flavoprotein fluorescence, lipofuscin autofluorescence, color photograph, OCT, dark adaptation (cone sensitivity, rode-cone break, rod sensitivity recovery slope), and choroidal flowmetry. Key secondary endpoint analyses include:

Change in rod intercept time from baseline assessed when all subjects have completed 18 months Change in rod intercept time from baseline assessed when all subjects have completed 24 months Mean intensity of flavoprotein fluorescence. The OcuMet Beacon (OcuMet Beacon, OcuScience Inc., Ann Arbor, Mich.) measures the flavoprotein fluorescence (FPF) of retinal tissue. The FPF signal has been shown to correlate with the metabolic state of mitochondria in retinal tissue. The average intensity of FPF in grayscale units (gsu) and the average curve width can be used as a functional measure to distinguish the level of tissue dysfunction compared to baseline measures and control subjects. Five FPF images, centered on the fovea, are obtained from the treatment eye. FPF images, stored as 512×512 pixel files, are analyzed to produce histograms. The histograms of pixel intensities, ranging from 0 to 65,536 grayscale units, are plotted for the treatment eye to yield an average gray scale unit waveform. The flavoprotein fluorescence pictures are taken at the baseline, and after 6, 12, 18, and 24 months of treatment. Analysis is performed in a masked fashion utilizing computer science expertise in development at OcuScience, Inc.

Mean intensity of lipofuscin fluorescence: Lipofuscin is derived from the lysosomal degradation of lipids, and its accumulation within the retinal pigment epithelium (RPE) is a useful marker of RPE disease and photoreceptor degeneration. Conversely, loss of lipofuscin fluorescence may be a sign of geographic atrophy in AMD as RPE cells are lost. Therefore, fundus autofluorescence may serve as a useful method of monitoring disease progression in AMD. Like quantification of flavoprotein fluorescence, histograms of pixel intensities are plotted for the treatment eye to yield an average gray scale unit waveform. In addition, geographic atrophy is observed qualitatively. Lipofuscin fluorescence images are obtained at the screening, baseline, and after 6, 12, 18, and 24 months after treatment.

Mean retinal thickness by optical coherence tomography. The difference between groups in mean change from baseline is tested using an analysis of covariance model where treatment assignment is a fixed factor and the baseline rod intercept is a covariate. Summaries provide results for both observed cases and with last observation carried forward. Spectral domain OCT (Heidelberg Spectralis, Heidelberg Engineering Inc., Heidelberg, Germany) allows for a cross-sectional image of the central macula to a resolution of approximately 5 microns. Post-imaging analysis will quantify the central retinal thickness, integrity of the inner segment/outer segment (IS/OS) disruption, presence of vitreous traction, choroidal thickness with enhanced depth imaging, and the presence of a choroidal neovascular membrane or pigment epithelial detachment. OCT is taken at the screening, baseline, and 6, 12, 18, and 24 months after treatment.

1. An ophthalmic composition, comprising:
    a pharmaceutically active drug comprising hydralazine in an amount between about 0.02-2 wt %;
    an acetate buffer solution having pH of between 3.9-4.5 in an amount between 8-12 wt %;
    propylene glycol in an amount between 0.5-2 wt %;
    sodium chloride in an amount between 0.25-1 wt %;
    methylparaben in an amount between 0.015-0.06 wt %;
    benzalkonium chloride in the form of a 50% solution, present in an amount between 0.01-0.04 wt %; and
    edetate disodium in an amount between 0.008-0.030 wt %;
    wherein said composition has a pH of between 4.0-4.4.

2. The composition of embodiment 1, wherein the drug is hydralazine hydrochloride.

3. The composition of the single or combined embodiments 1 or 2, wherein the drug is present in an amount between 0.5-2 wt %.

4. The composition of the single or combined embodiments 1-3, wherein the acetate buffer solution has a pH of 4.2 and is present in an amount of 10 wt %.

5. The composition of the single or combined embodiments 1-4, wherein the acetate buffer solution is comprised of sodium acetate and 2N acetic acid.

6. The composition of the single or combined embodiments 1-5, wherein propylene glycol is present in an amount of 1 wt %.

7. The composition of the single or combined embodiments 1-6, wherein methylparaben is present at 0.03 wt %.

8. The composition of the single or combined embodiments 1-7, wherein benzalkonium chloride in the form of a 50% solution is present at 0.02 wt %.

9. The composition of the single or combined embodiments 1-8, wherein edetate disodium is present at 0.015 wt %.

10. A method for preparing an ophthalmic formulation, comprising:
    mixing water and an acetate buffer solution having a pH 3.9-4.5 to form a first interim mixture, the acetate buffer solution added in an amount to provide between about 8-12 wt % of acetate buffer solution in the formulation;
    adding to the first interim mixture edetate disodium, to form a second interim mixture, the edetate disodium added in an amount to provide between about 0.008-0.030 wt % of edetate disodium in the formulation;
    adding to the second interim mixture propylene glycol to form a third interim mixture, the propylene glycol added in an amount to provide between about 0.5-2 wt % of propylene glycol in the formulation;
    adding to the third interim mixture sodium chloride to form a fourth interim mixture, the sodium chloride added in an amount to provide between about 0.25-1 wt % of sodium chloride in the formulation;
    adding to the fourth interim mixture benzalkonium chloride to form a fifth interim mixture, the benzalkonium chloride added in an amount to provide between about 0.01-0.04 wt % of benzalkonium chloride in the formulation; and
    adding to the fifth interim mixture methylparaben to form a sixth interim mixture, the methylparaben added in an amount to provide between about 0.015-0.06 wt % of methylparaben in the formulation;
    adding to the sixth interim mixture to form said formulation, a pharmaceutically active drug comprising hydralazine.

11. The method of embodiment 10, wherein one or more of the steps of adding comprise mixing while adding.

12. The method of the single or combined embodiments 10-11, wherein the acetate buffer solution is added in an amount to provide 10 wt % acetate buffer in the formulation.

13. The method of the single or combined embodiments 10-12, wherein the acetate buffer solution is comprised of sodium acetate and 2N acetic acid.

14. The method of claim the single or combined embodiments 10-13, wherein edetate disodium is added in an amount to provide 0.015 wt % edetate disodium in the formulation.

15. The method of the single or combined embodiments 10-14, wherein propylene glycol is added in an amount to provide 15 wt % propylene glycol in the formulation.

16. The method of the single or combined embodiments 10-15, wherein sodium chloride is added in an amount to provide 0.5 wt % sodium chloride in the formulation.

17. The method of the single or combined embodiments 10-16, wherein benzalkonium chloride is added in an amount to provide 0.02 wt % benzalkonium chloride in the formulation.

18. The method of the single or combined embodiments 10-17, wherein methylparaben is added in an amount to provide 0.03 wt % methylparaben in the formulation.

19. The method of the single or combined embodiments 10-18, wherein the pharmaceutically active drug is hydralazine present in the formulation at between 0.5-2 wt %.

20. A method for treating macular degeneration, comprising: administering to an eye of a subject at risk of or diagnosed with macular degeneration, an ophthalmic composition according to any one of claims 1-9 or the formulation prepared according to the method of claims 10-19.

21. The method of embodiment 20, wherein said macular degeneration is age-related dry macular degeneration.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. An ophthalmic composition, consisting essentially of:
   a pharmaceutically active drug comprising hydralazine in an amount between about 0.02-2 wt %;
   an acetate buffer solution having pH of between 3.9-4.5 in an amount between 8-12 wt %;
   propylene glycol in an amount between 0.5-2 wt %;
   sodium chloride in an amount between 0.25-1 wt %;
   methylparaben in an amount between 0.015-0.06 wt %;
   benzalkonium chloride in the form of a 50% solution, present in an amount between 0.01-0.04 wt %; and
   edetate disodium in an amount between 0.008-0.030 wt %;
   wherein said composition has a pH of between 4.0-4.4;
   wherein a decrease in the w/w % of the active drug is less than about 10% after one month storage.

2. The composition of claim 1, wherein the drug is hydralazine hydrochloride.

3. The composition of claim 2, wherein the drug is present in an amount between 0.5-2 wt %.

4. The composition of claim 1, wherein the acetate buffer solution has a pH of 4.2 and is present in an amount of 10 wt %.

5. The composition of claim 4, wherein the acetate buffer solution is comprised of sodium acetate and 2N acetic acid.

6. The composition of claim 1, wherein propylene glycol is present in an amount of 1 wt %.

7. The composition of claim 1, wherein methylparaben is present at 0.03 wt %.

8. The composition of claim 1, wherein benzalkonium chloride in the form of a 50% solution is present at 0.02 wt %.

9. The composition of claim 1, wherein edetate disodium is present at 0.015 wt %.

10. A method for treating macular degeneration, comprising:
    administering to an eye of a subject diagnosed with macular degeneration, an ophthalmic composition according to claim 1.

11. The method of claim 10, wherein said macular degeneration is age-related dry macular degeneration.

12. The composition of claim 1, wherein a decrease in the w/w % of the active drug is less than about 1.0% after one month storage.

13. The composition of claim 1, wherein a decrease in the w/w % of the active drug is less than about 0.5% after one month storage.

14. The composition of claim 1, wherein the composition is stored at about 25° C.

15. The composition of claim 1, wherein the composition is stored at about 40° C.

* * * * *